(12) United States Patent
Whitehill et al.

(10) Patent No.: US 12,226,195 B2
(45) Date of Patent: Feb. 18, 2025

(54) SYSTEM AND METHODS FOR DETERMINING HEALTH-RELATED METRICS FROM COLLECTED PHYSIOLOGICAL DATA

(71) Applicant: Measure Labs, Inc., Seattle, WA (US)

(72) Inventors: Matthew Steven Whitehill, Seattle, WA (US); Jamien McCullum, Seattle, WA (US); Eric Chen, Seattle, WA (US); Jessie Young, Seattle, WA (US)

(73) Assignee: MEASURE LABS, INC., Seattle, WA (US)

( * ) Notice: Subject to any disclaimer, the term of this patent is extended or adjusted under 35 U.S.C. 154(b) by 267 days.

(21) Appl. No.: 17/815,891

(22) Filed: Jul. 28, 2022

(65) Prior Publication Data

US 2023/0036114 A1 Feb. 2, 2023

Related U.S. Application Data

(60) Provisional application No. 63/365,670, filed on Jun. 1, 2022, provisional application No. 63/226,541, filed on Jul. 28, 2021.

(51) Int. Cl.
*A61B 5/021* (2006.01)
*A61B 5/00* (2006.01)
(Continued)

(52) U.S. Cl.
CPC .......... *A61B 5/021* (2013.01); *A61B 5/14552* (2013.01); *A61B 5/4839* (2013.01); *A61B 5/486* (2013.01); *A61B 5/6898* (2013.01); *A61B 5/7221* (2013.01); *A61B 5/7267* (2013.01); *A61B 5/742* (2013.01); *A61B 5/746* (2013.01);
(Continued)

(58) Field of Classification Search
CPC ............ A61B 5/02416; A61B 5/02405; A61B 5/7221; A61B 5/742; A61B 5/0004; A61B 5/0295; A61B 5/14552
See application file for complete search history.

(56) References Cited

U.S. PATENT DOCUMENTS

2016/0143567 A1   5/2016   De Haan
2019/0142288 A1   5/2019   Aliamiri
(Continued)

FOREIGN PATENT DOCUMENTS

WO   2018112613   6/2018
WO   2019082203   5/2019

*Primary Examiner* — Gerald Johnson
(74) *Attorney, Agent, or Firm* — Summit Patents PC

(57) ABSTRACT

Techniques and systems include predicting various health conditions using a photoplethysmography (PPG) signal or a video signal based on images of a patient's fingertip or other body portion captured using a mobile device. The video signal may be transformed into a pseudo PPG signal to measure blood volume changes in the patient's blood flow to derive data indicating a disease state or health-related characteristic, such as blood oxygen level, blood glucose level, heart rate variability, hemoglobin, respiration rate, or arrhythmia. Techniques involve real-time environment assessment and problematic issue detection, training an artificial intelligence (AI) model to measure signal quality so as to select high-quality signals from a range of signals, and domain adaption and transfer learning to make use of publicly available datasets.

20 Claims, 11 Drawing Sheets

(51) Int. Cl.
*A61B 5/1455* (2006.01)
*A61B 5/024* (2006.01)

(52) U.S. Cl.
CPC ... *A61B 5/02416* (2013.01); *A61B 2560/0223* (2013.01); *A61B 2560/0431* (2013.01); *A61B 2562/0219* (2013.01)

(56) References Cited

U.S. PATENT DOCUMENTS

| | | |
|---|---|---|
| 2019/0357855 A1 | 11/2019 | Sinha |
| 2020/0100693 A1* | 4/2020 | Velo ........................ G16H 50/20 |
| 2020/0205745 A1 | 7/2020 | Khosousi |
| 2021/0007617 A1 | 1/2021 | Kim |
| 2022/0104737 A1 | 4/2022 | Smit |
| 2022/0263907 A1 | 8/2022 | Nair |
| 2022/0361788 A1 | 11/2022 | Shah |

\* cited by examiner

SYSTEM AND METHODS FOR DETERMINING HEALTH-RELATED METRICS FROM COLLECTED PHYSIOLOGICAL DATA

CROSS REFERENCE TO RELATED APPLICATIONS

This application claims priority and benefit from the U.S. Provisional Patent Application 63/226,541, filed Jul. 28, 2021, and titled, "System and Methods for Determining Health-Related Metrics from Data Collected by a Mobile Device," which are incorporated herein by reference in their entirety for all purposes.

BACKGROUND

There are several quantities that are regularly measured and evaluated to provide information about a person's health. These quantities and both their real-time values and trends over various timescales can sometimes be used as indications of disease or a serious health condition. Examples of such quantities that may be used to monitor and, in some cases, diagnose a health condition include blood pressure, pulse or heart rate, and blood oxygen saturation (SpO2), among other biomarkers. Conventionally, such health-related quantities are measured at a health clinic, the office of a provider of medical services, or with special equipment that is used in the home.

However, these conventional methods of measuring health quantities are not always available, may require advance planning to use, and are not convenient for situations where a person is engaging in activities away from home. Further, the conventional methods provide a "snapshot" in time of the values of the health-related quantities but may not provide sufficient data or data collected at a sufficient time or set of times to detect or diagnose a health condition. For example, a physician or paramedic may want to know a person's blood pressure over a time interval around when they suffered some type of pain. This may be difficult to do without the person being in a location where someone can make those measurements. As another example, a person may want to monitor how their blood pressure responds to certain activities or behaviors, and such monitoring may be difficult to do outside of their home.

Although there are some portable devices that can be used to monitor blood pressure, these typically are not as accurate as desired. Further, although portable blood pressure monitors are available, these typically require that a person be in a situation where a "cuff" may be used to obtain the blood pressure reading, and this is not always possible or convenient.

What is desired are systems, apparatuses, and methods for enabling a person to monitor one or more of their health-related quantities more conveniently using a ubiquitous computing device and without having to be at a particular location.

BRIEF DESCRIPTION OF THE DRAWINGS

The disclosure will be understood more fully from the detailed description given below and from the accompanying figures of embodiments of the disclosure. The figures are used to provide knowledge and understanding of embodiments of the disclosure and do not limit the scope of the disclosure to these specific embodiments.

DETAILED DESCRIPTION

Figure 1:
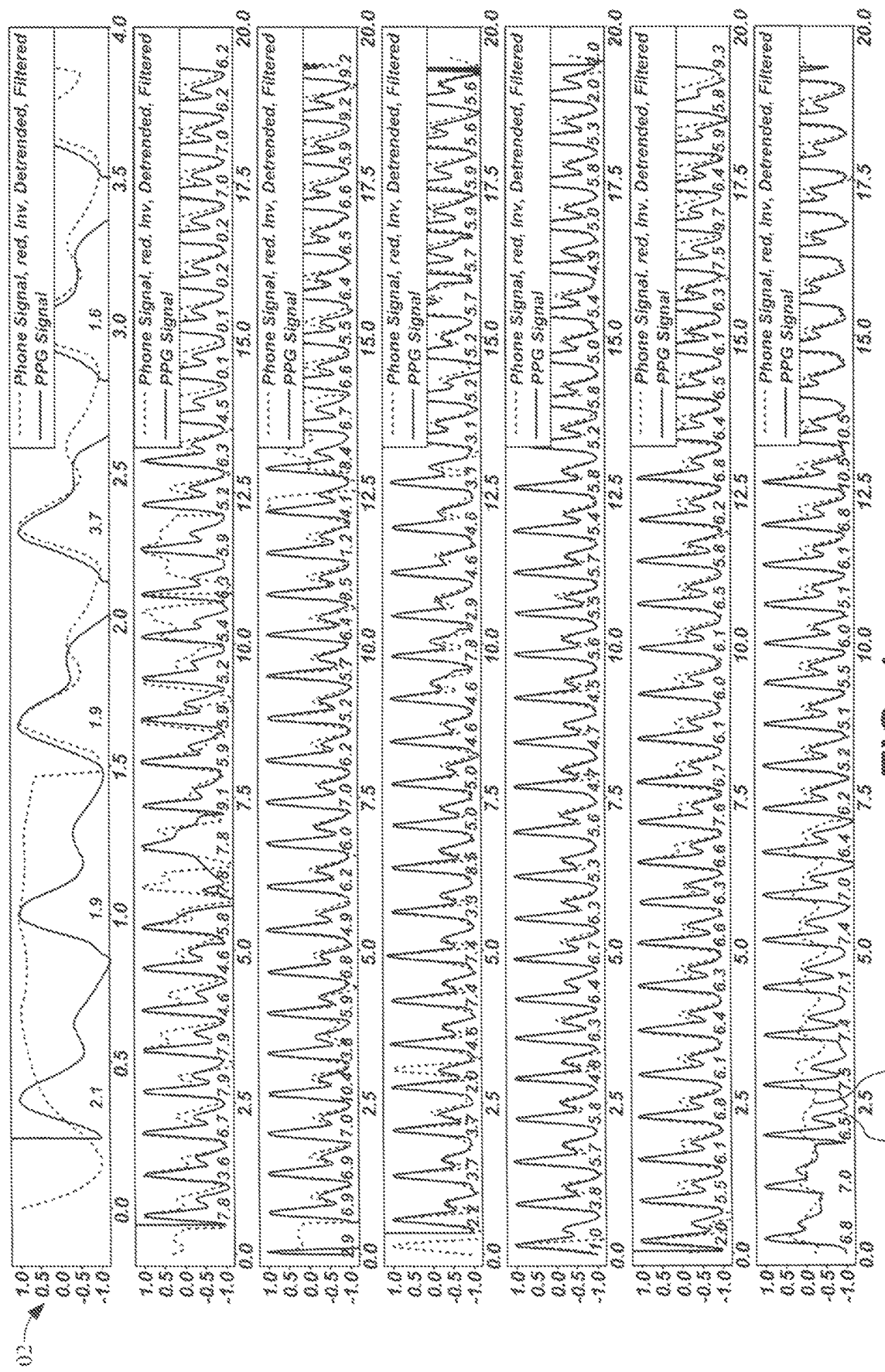
FIG. 1 illustrates example photoplethysmography (PPG) signal waveforms and a comparison between a PPG signal obtained from a pulse oximeter and a signal derived from the red channel of an RGB video signal, according to some embodiments.

Photoplethysmography (PPG) is an optical technique used to detect volumetric changes in blood in peripheral circulation, using low-intensity infrared (IR) light. When light travels through biological tissues it is absorbed by bones, skin pigments, and both venous and arterial blood. Since light is more strongly absorbed by blood than surrounding tissues, changes in blood flow can be detected by PPG sensors as indicated by changes in the transmitted intensity of light. A voltage signal from PPG sensors may be proportional to the quantity of blood flowing through blood vessels. Even small changes in blood volume can be detected using this method. A PPG signal has several components including volumetric changes in arterial blood that is associated with cardiac activity, variations in venous blood volume that modulates the PPG signal, and a DC component showing the tissues' optical properties and subtle energy changes in the body.

This disclosure describes a number of techniques and systems for determining or predicting various health conditions. The techniques and systems involve use of an optical signal, such as a PPG signal or a video signal transformed into a pseudo PPG signal, to measure blood volume changes in a patient's blood flow to derive data indicating a disease state or biomarker. In the past, an optical signal used for this purpose generally suffered from quality and inconsistency issues, even in a controlled environment on the same patient.

Previous efforts to derive blood pressure from smartphone-sourced PPG have shown promising results in lab settings but have not reached good enough accuracy in real-world settings for widespread adoption. A substantial technical barrier to achieving sufficient real-world accuracy is the handling of the inconsistency and quality of these PPG signals created under a diversity of conditions set forth by sensors (e.g., camera hardware, numerous flash settings), users (e.g., body weight, skin tone, ages), and environments (e.g., contact grips, lighting conditions). There is no canonical "ground truth" PPG, since even purpose-built PPG devices in controlled environments may produce different signals for the same subject by small changes in placement or orientation of the device.

Machine learning (ML) has been used to attempt to address the issues and complexity described above. Traditional ML methods such as a Support Vector Machine (SVM) algorithm or regression have shown promising results but require perhaps more than fifty or so features extracted by hand, even when using PPG signals from purpose-built devices in controlled environments. In recent years, neural networks have been used in different ways to successfully improve performance, especially with smartphone-sourced PPG. But what has been achieved in this way is still insufficient due to the large diversity of signals and expensive, limited training data. One common theme is that poor signals are often thrown out during training and are not considered during inference, leading to many failed or inaccurate readings. Another common theme is that models may work only on a limited number of smartphones or other devices.

Embodiments described herein address the problems discussed above and may achieve real-world accuracy with even just limited data. The embodiments involve real-time environment assessment and problematic issue detection, training an AI model to measure signal quality so as to select high-quality signals among signals having a range of qualities, and domain adaption and transfer learning to make use of publicly available datasets, just to name a few examples.

In particular, embodiments described herein are directed to systems, methods, and apparatuses for more conveniently and accurately measuring and monitoring one or more health-related characteristics, including but not limited to blood pressure and heart rate, for example. In some embodiments, the health-related characteristics may include blood oxygen level, blood glucose level, hemoglobin A1C, heart rate variability, hemoglobin, respiration rate, blood oxygen, or arrhythmia.

One embodiment is directed to a method for determining one or more health-related quantities for a person based on video images captured using a mobile device (e.g., a smartphone). The method may include steps, stages, or operations that include activation or launch of an application hosted by the mobile device, or the application may be a web-based application (e.g., wherein a web link leads to a web page on a browser of a mobile device), and collecting a sample or samples of video of a person's fingertip or other tissue. For example, during data collection, participants may have equipment placed on them, such as a pulse oximeter placed on the finger, toe, and/or earlobe, a single-lead Electrocardiogram (ECG), or an Inertial Measurement Unit (IMU) taped to the sternum. Collection of data from these sensors may include a participant's blood pressure, which may be taken using the auscultation method (e.g., using a stethoscope to listen for Korotkoff sounds).

The method may also include processing the collected sample(s) to approximate a PPG signal and detection of possible data collection problems during acquisition of user data, which can occur under normal use in diverse conditions. The method may further include evaluating quality of the PPG signal that may have been gathered from diverse subjects and cameras under diverse conditions and passing the PPG signal as input to a trained blood pressure AI model.

The activation or launch of the application may involve the application setting collection parameters and equipment characteristics, such as device manufacturer and model, camera or video settings, lens, or video processing options, and so on. For example, in some implementations, camera settings, such as for exposure settings, may be determined from values i) stored in a computer memory, ii) from a binary search, or iii) based on intelligent search modes. If needed, in some embodiments, the application may collect data regarding the patient, such as skin tone, and other data regarding local environment, lighting conditions, stability/motion of device, and so on, before beginning video capture. Collecting a sample or samples of video from a patient's fingertip (or other tissue) using a mobile device may involve use of the application's user interface (UI) to guide a user (e.g., the patient) in the placement of their fingertip and in holding the mobile device correctly and steadily to collect the data. A camera (and flash LED) of a mobile device, such as a smartphone, or other portable device may be used. In some implementations, various features of the patient may be utilized to improve biomarker estimation. These features provide additional context to allow the AI model to make a more accurate prediction. These features may include demographics about the patient (e.g., age, sex, height, weight, etc). For example, the shape (e.g., features) of a PPG signal may indicate conditions that are different between an old person and a young person. In a specific example, a PPG signal without a dicrotic notch is generally normal for an older person but the same signal may indicate relatively high BP for someone who is younger, or taller.

In some implementations, the application may perform a biomarker calibration (e.g., a baseline). For example, biomarker calibration may involve taking a PPG measurement and a biomarker measurement at the same time, then entering the biomarker measurement into the application as a "calibration value" for the corresponding PPG measurement. An AI model may then use this information during a measurement process. Thus, the AI model may receive the biomarker measurement, the calibration PPG signal (e.g., based on the calibration value), and current PPG signal. The process may combine this information in the AI model to analyze the PPG signals and to subsequently estimate a biomarker, for example.

Processing the collected sample(s) to approximate a PPG signal may involve a PPG signal generator module or similar functionality that may continuously process raw camera frames by extracting average red (R), green (G), and blue (B) values of all the RGB pixels in each video frame. In some implementations, the red channel is taken to approximate the PPG signal. Obtained red channel signals may be smoothed using a Butterworth filter or other filter and up-sampling may be performed using linear interpolation, for example. A Butterworth filter is a type of signal processing filter designed to have a frequency response as flat as possible in the passband. It may also be referred to as a maximally flat magnitude filter.

In some implementations, data collection problems (problematic issues) during acquisition of user data may be detected. Such problems may occur under normal use in diverse conditions. In other words, issues or factors that could result in unreliable or unusable data may be detected. For example, ambient conditions or factors may include motion of camera (e.g., relative to finger), movement of finger (e.g., relative to camera), improper position of finger, and a change in lighting that impacts an ability to accurately and reliably extract a PPG-like signal from camera frames. An Issue Detector module or such functionality may be included in the system architecture, as described below. Although examples described herein involve a fingertip, other tissue or parts of the body may be used instead of, or in addition to, the fingertip. Claimed subject matter is not limited in this respect.

Camera settings may be adjusted to get a "good" (e.g., acceptable) signal during diverse conditions (ambient lighting, skin tone of user, mobile device camera, etc.). In some implementations, previously measured or entered skin tone information of a user may be retrieved from memory of the user's mobile device. An output that includes a determined disease state or a biomarker may be modified based on the retrieved skin tone information. In some embodiments, to at least partially control ambient factors/conditions, an Environment Assessor module may step up the light sensitivity periodically (e.g., every 1.2 seconds), subsequently holding constant the light sensitivity when the red channel intensity, for example, from the camera frames reach a minimum (predetermined) threshold. The Environment Assessor module may also adjust the intensity of light emitted by a flash LED system of the camera.

Evaluating the quality of the PPG signal gathered from diverse subjects and cameras under diverse conditions may involve identifying individual pulses in the PPG signal. For example, in one embodiment, a Pulse Generation module or such functionality able to detect signal amplitudes, may identify a peak or valley that expresses an individual pulse in the PPG signal. A signal quality evaluation process may reject or remove from further processing pulses that fail to meet the threshold required for processing and evaluation. In one embodiment, a Signal Quality Assessor module may be a neural network trained to assess individual pulses. During training of the Signal Quality Assessor module, collected fingertip (or other tissue) data may be manually annotated (described below) with an "acceptable" or "not acceptable" label to produce training data for a model. For example, an "acceptable" pulse is uniform (multiple pulses are consistent among themselves) and has the characteristics of a PPG signal (e.g., generally having a steep slope up to a relatively sharp peak and having zero or up to 2 smaller notches on the way down). In some implementations, the Signal Quality Assessor may compare mobile device-captured PPG signals to Pulse Oximeter-captured PPG signals, which may be considered a "ground truth" PPG via a cross-correlation algorithm. In some implementations, rather than using a trained neural network, a cross correlation process may be used to compare individual pulses to a set of canonical pulses that are considered to represent all the different shapes of pulses that are likely to occur. Such canonical pulses may be identified manually, for example. The cross correlation process may involve overlaying a pulse on a group of "good" pulses and tracking the highest value of correlation to any of these good pulses. This process can help determine whether the pulse has a "PPG-like" shape (e.g., has features and characteristics that are the same as or similar to that of an actual PPG pulse). In contrast, an auto correlation process may involve overlaying a current pulse on a previous pulse and the subsequent pulse. The process may average the correlation between both values. In other examples, the process may overlay a current pulse with more than one neighboring pulses (e.g., five prior pulses and five subsequent pulses).

Based on environmental and signal quality conditions (during signal acquisition), and an absence of data acquisition problems, the PPG pulses may be passed as input to a trained AI blood pressure model. In one embodiment, the blood pressure model is a neural network that continuously takes in "acceptable"-quality pulses from the PPG signal as input and produces systolic BP and diastolic BP as output. The model averages the produced systolic and diastolic BP values to produce final BP values that are returned to the user.

As mentioned above, techniques that may achieve real-world accuracy may involve training an AI model to measure signal quality so as to select high-quality signals from signals having a range of qualities. In one embodiment, an AI model training process may involve, due to limited training data, a base model that is trained on publicly available, synchronized, PPG and BP datasets. The trained base model may be used as a basis for continued training using learning on collected (e.g., historical) pulse oximeter PPG, smartphone fingertip video, and blood pressure data, as described below. A smartphone-sourced PPG signal produced from fingertip videos may also be used by applying a Butterworth filter, and up-sampling the pulse oximeter PPG and smartphone-sourced PPG to match the frequency of the publicly available data using linear interpolation, for example.

Additional AI training data may be captured for use in training the base model, such as from users of the application, training data collected under controlled conditions, and continuous data acquisition and model training through data collection along with accurate measurement of health quantity using a separate device(s). When in use, data collection and processing may be performed on a user's device, wherein the user may maintain privacy.

Output from the trained AI model may provide information representing a measure of one or more of the person's blood pressure, heart rate, SpO2, or other health-related quantity. Based on the model output, one or more tasks may be executed by an application hosted by a mobile device, such as providing results via an application programming interface (API) call back that enables a developer to use the data in their own application, showing trends in the measured quantities over time, tuning medication dosages based on changes in the measured quantities, placing the measured data into an electronic health record (EHR) for use by a physician, and statistically analyzing the measured data in conjunction with other data or information (such as sleep quality, stress, or anxiety levels, etc.). Other tasks that may be performed by a mobile device, for example, may include generating an alert to a user that a measured quantity exceeds a preset threshold value, wherein the average value of a measured quantity exceeds the preset value over a set time period, and wherein the measured value in combination with another aspect of the user (BMI, weight, blood glucose level, etc.) suggests a problem needing attention. Still other tasks may include generating a phone call to an emergency number if a measured quantity alone or over time exhibits a characteristic of serious medical problem (such as stroke, etc.) and generating a recommendation to engage in an activity, undertake a change in behavior, etc.

As described above, in various embodiments, biomarkers may be estimated from biosensor data, which may be an optical signal like a PPG, electrical signals like an ECG, and so on. The optical biosensor data may be acquired from a smartphone-captured video of a person's finger or from a PPG sensor in devices such as a pulse oximeter. For example, measurements of real-time blood pressure and heart rate data may be acquired via fingertip video obtained with a mobile device. In an implementation, the mobile device may include a data measurement module (DMM), which may comprise a software development kit (SDK) embedded into an operating system of the mobile device. A user may use the mobile device (e.g., a smartphone, wrist-worn wearable such as smartwatch or smart wristband, earbud, or tablet) to measure their blood pressure and heart rate, for example, by operating the DMM, which may navigate the user to a particular view (e.g., menu of options and/or instructions) on the smartphone. The user may place their fingertip against the lens of the mobile device camera, and after about a minute or so, for instance, the DMM may provide the user's blood pressure and heart rate data to an application on the mobile device or external to the mobile device. In some implementations, video frames and related data may be processed completely on the device so that user identities may be completely unknown outside the device, for anonymity.

In some embodiments, the DMM works by extracting the red channel from each frame of the fingertip video to form a PPG signal. As explained above, PPG is commonly used in methods for measuring blood volume changes and can be used to derive health measures like heart rate, Sp02, and blood pressure. A neural network may be used to extract these health measures from the smartphone signal produced by the DMM.

FIG. 1 illustrates example PPG waveforms 102 and illustrates the similarity between a PPG signal 104 obtained from a pulse oximeter and a red channel signal 106 derived from the red channel of a video signal captured by a smartphone or other similar portable device. As can be seen from the figure, the red channel signal 106, which corresponds with blood flow in the fingertip, is close to and mimics the behavior of PPG signal 104 when environment and signal quality are adequately controlled. This allows for the red channel signal being a suitable substitute for an actual PPG signal and provides a basis for which signal capture and signal quality techniques described herein are utilized.

Figure 2:
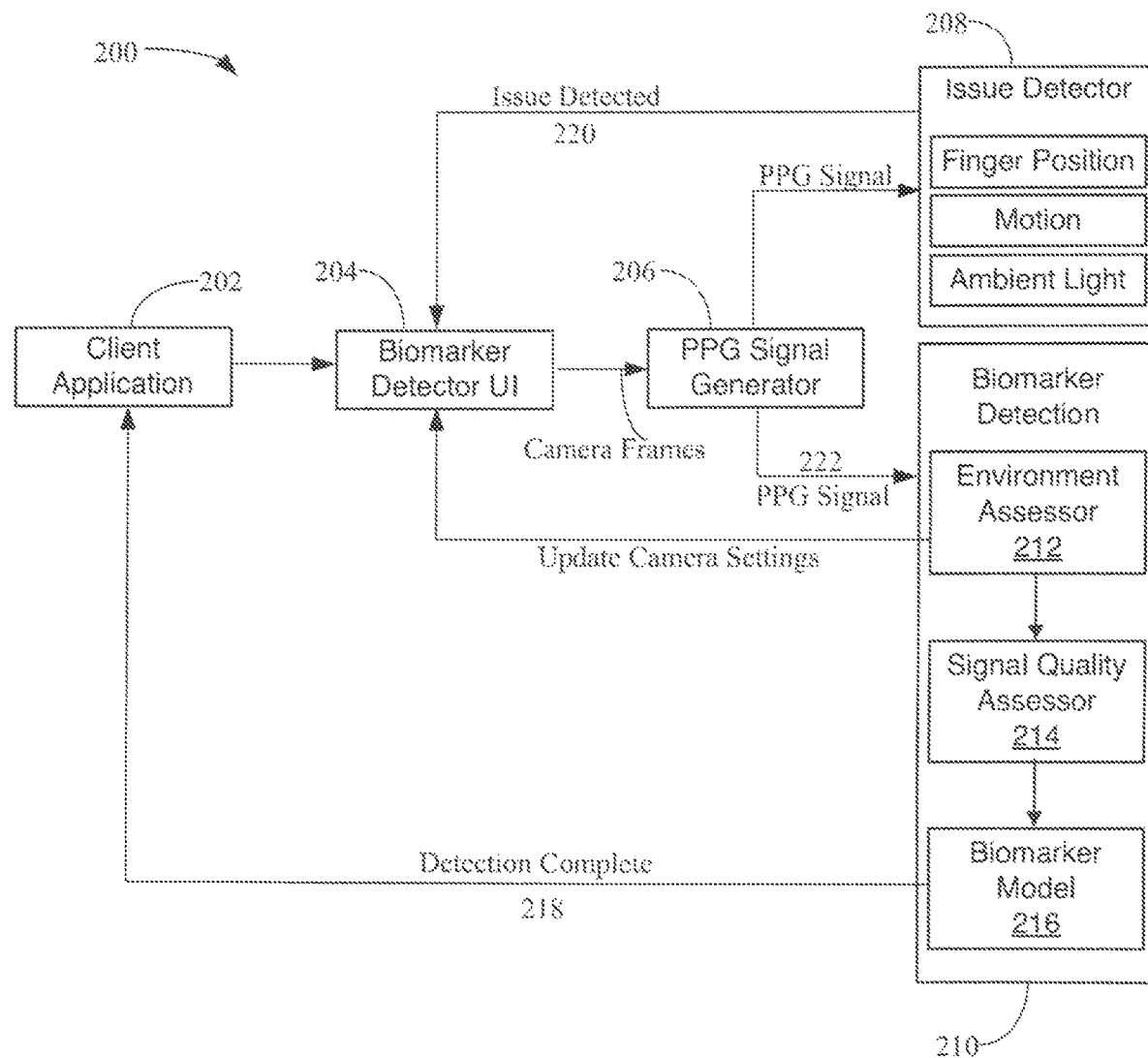
FIG. 2 is a block diagram illustrating a process flow and functional elements that may be used in implementing various embodiments.

FIG. 2 is a block diagram of a system 200, illustrating a process flow and components that may be used in implementing an embodiment of the disclosed methods. For example, system 200 may be a DMM that includes subsystems, elements, components, or modules that implement functionality for measuring blood pressure, among other biomarkers. Specifically, system 200 may include a client application 202, a Biomarker (e.g., BP) Detector user interface (Biomarker Detector UI) 204, a PPG Signal Generator 206, an Issue Detector 208, and a Biomarker (e.g., BP) Detection module 210.

Client application 202 may comprise computer-executable instructions that are installed on a user's device, which may be a mobile device such as a smartphone, wrist-worn wearable such as smartwatch or smart wristband, earbud, or tablet. In some embodiments, the application uses APIs to integrate functionality for measuring blood pressure or other health-related quantities with the capabilities of the mobile device. Client application 202 may use the APIs to navigate to a user interface associated with a video/data collection service and to provide blood pressure values when complete. In some embodiments, client application 202 may be developed using an SDK that is provided to enable access to, and use of, models and data processing methods, described below.

Biomarker Detector UI 204 is a user interface component that guides (e.g., provides real-time instructions for) the user in measuring their blood pressure or other biomarkers. Biomarker Detector UI 204 (and underlying services or functions) may provide tools to enable the user to initiate the video/data collection used to determine their blood pressure and/or provide a mechanism to interact with other features or functionality of system 200 and methods described herein. For example, the Biomarker Detector UI may display a view that provides instructions and shows feedback to the user, captures camera frames, and continuously or periodically passes the frames to PPG Signal Generator 206. For example, Biomarker Detector UI 204 may guide the user in placing their fingertip correctly on the camera, holding the smartphone correctly and steadily, and may provide the user with measurement progress and may indicate any errors in the process. Biomarker Detector UI 204 may keep the camera flash LED on, and may control its intensity, to illuminate the finger during image capture.

Biomarker Detector UI 204 may be part of a service or application that interacts with Issue Detector 208 to control the acquisition of video/data and processing of the acquired video/data into a PPG signal by PPG Signal Generator 206. In some embodiments, Biomarker Detector UI 204 may be provided as a part of an SDK. In some embodiments, Biomarker Detector UI 204 may allow for measurements of a different health-related quantity (e.g., other than, or in addition to, blood pressure). PPG Signal Generator 206 may provide PPG signals to Issue Detector 208 and Biomarker Detection module 210.

A blood pressure detection process, performed by Biomarker Detection module 210, may begin once no issues (e.g., as determined by Issue Detector 208) have been identified during an initial time period, such as the first five seconds of the process, for example. A PPG signal may be passed through the following components to produce blood pressure: an Environment Assessor 212, a Signal Quality Assessor 214, and a Biomarker model 216. There generally may be many variables that impact the quality of the PPG signal that in turn impact the accuracy of BP readings. Such variables may include ambient lighting conditions, skin tone, and smartphone camera quality. To control for this, Environment Assessor 212 may hold constant the light sensitivity and shutter speed of the camera of the mobile device at values that produce a minimum threshold of intensity. In some implementations, Environment Assessor 212 may step up the light sensitivity periodically, such as every 10 seconds, for example. In another implementation, Environment Assessor 212 may step up the light sensitivity by 75 ISO every 1.2 seconds, locking the light sensitivity when the red channel intensity from the camera frames reaches a minimum threshold of 120. These values (e.g., 75 ISO and 1.2 s) may be determined empirically to increase the red channel intensity as fast as possible while stabilizing at each increment. Claimed subject matter is not limited to such values.

An updated PPG signal with camera settings (e.g., as metadata, such as time stamp of image capture, exposure time, aperture, resolution, and so on) are passed through Signal Quality Assessor 214, which may produce individual pulses from signals passed from Environment Assessor 212 and may pass acceptable pulses to Biomarker model 216. In one embodiment, Signal Quality Assessor 214 is a neural network trained to assess individual pulses. Training data may be manually annotated based on collected user fingertip data with a label of "acceptable" or "not acceptable" to produce training data for this model. In general, an "acceptable" pulse is uniform (consistent with other pulses) and has the characteristics of a PPG signal (generally a steep slope up to a relatively sharp peak and has 0 to 2 smaller notches on the way down), though claimed subject matter is not so limited.

In some implementations, functions of Signal Quality Assessor 214 and Biomarker Model may be combined. For example, rather than having these two entities separate, a single model may be trained using the same annotated data to do both tasks using multi-task training. This single model approach may help the Signal Quality Assessor determine what features work better for a biomarker model, such as a blood pressure model, and may lead to improved accuracy.

Biomarker model 216, which is a neural network, may depend on relatively high quality signals to produce a good result. In some implementations, a time-series of image frames of video are partitioned into video chunks (e.g., segments) that each have a predetermined time span. Accordingly, Signal Quality Assessor 214 looks at such chunks of signals provided by Environment Assessor 212 and only passes acceptable signals to Biomarker model 216. For example, such chunks of signals may be two-second long segments of a PPG signal. In some implementations, two contiguous video chunks may be combined into a video segment having a portion that comprises an overlap between the two contiguous video chunks. Signal Quality Assessor 214 may generate a quality score determined by comparing a signal quality feature of a PPG signal provided to Biomarker Detection 210 to a same-type signal quality feature of a deep learning-based model PPG signal, which may be stored in computer memory or updated and provided by Biomarker Model 216, for example. In other implementations, Signal Quality Assessor 214 may generate a quality score based on metadata included in the PPG signal provided to Biomarker Detection 210.

In some implementations, rather than using a trained neural network, particular features may be extracted from a pulse(s). For example, such features may be about the morphology of a pulse such as landmark points (e.g., the timing and amplitude of the systolic peak), derivative-based features, slopes of the rises and falls within the pulse, frequency-domain features, wavelet-based features, and so on. Such features may be fed to a machine learning model such as linear regression, support vector regression (SVR), decision tree (e.g., random forest), or multi-layer perceptron (fully connected deep learning layers) to predict blood pressure. Methods for optimizing the features and models may also be used, such as determining feature importance, genetic algorithms, or ensembles of models, for example.

In some implementations, Signal Quality Assessor 214 is a neural network trained to assess chunks of PPG signals. Biomarker Model 216 may produce a systolic BP and diastolic BP as output. The model may average the produced systolic and diastolic BP values to produce final BP values that are returned to the user. After acceptable PPG/red channel signals have been processed, the blood pressure values may be provided to the user through client application 202. In some embodiments, the blood pressure values, peak values, changes over time, and so on may be used as input data to a set of rules or a trained model to determine whether to generate an alert, place a call to a medical provider, recommend an activity or change in behavior to the user, etc. In some embodiments, Biomarker model 216 is based, at least in part, on a neural network that is trained using transfer learning on pulse oximeter PPG data and information collected or produced by a mobile device hosting client application 202, as described below. Such information may include video chunks or blood pressure data previously determined by the mobile device, for example.

In some embodiments, as mentioned above, fingertip data, such as in the form of PPG segments, may be annotated (automatically or manually) as being "acceptable" or "not acceptable" to produce training data for Biomarker model 216, which is a neural network that continuously or periodically takes in as input, "acceptable"-quality, segments (e.g., two-second long chunks) of the PPG signal and produces systolic BP and diastolic BP as output. Biomarker model 216 may average the produced systolic and diastolic BP values to produce final BP values that are returned to the user. In some implementations, the training process for the Biomarker model 216 may be performed by first training a base model on publicly available, synchronized, PPG and biomarker datasets. The trained base model may continue to be trained using transfer learning on pulse oximeter PPG, smartphone fingertip video, and blood pressure data subsequently collected. The smartphone PPG may be produced from fingertip videos in a similar process on the mobile device. For example, this process may include using red channel data of a PPG, applying a Butterworth filter, and up-sampling pulse oximeter PPG and smartphone PPG to match the frequency of the publicly available data using linear interpolation.

PPG Signal Generator 206 may receive video frames collected by a camera in the user's device and may perform the signal/image processing to generate the PPG/red channel signal for further analysis and evaluation. For example, PPG Signal Generator 206 may continuously or periodically process raw image frames by extracting the average red, green, and blue pixel values across an array of pixels in each frame. In some implementations, a single image frame at a time is processed. In other implementations, two or more image frames are processed at a time. The red values may be smoothed with a Butterworth filter and up-sampled via linear interpolation for Biomarker model 216. Such processed frames and associated PPG signal may be passed to the UI of client application 202 as "detection complete," as indicated by arrow 218.

Issue Detector 208 may be responsible for implementing a set of processes to determine if the video/data collection should be interrupted, stopped, or discarded due to unreliability caused by one or more of the user's finger position, motion of the camera or user's finger, or ambient light conditions, among other possible sources of error. Patient physiological data, in the form of a PPG signal, for example, may include metadata, which may be measured by an IMU of the camera, or other elements that may be used as signal quality features. For example, the IMU (and thus the metadata) may provide measurements (e.g., spatial coordinates, orientation, acceleration, and so on) for generating motion signatures or such measurements may be represented by motion signatures. The patient physiological data, which may also include a disease state or a biomarker feature, may be provided to Issue Detector 208 from PPG Signal Generator 206, for example. Signal quality features and disease state or biomarker features may be manifested as characteristics or parameters of the PPG signal, for example. For example, a PPG signal having such characteristics and parameters may be provided to Issue Detector 208 to determine signal quality (e.g., a quality score) or whether problematic issues occurred during the measurement process that led to the PPG signal. The PPG signal having such characteristics and parameters may also be provided to Biomarker Detection 210 to determine a disease state or biomarker. For example, a process for determining the disease state or biomarker of patient physiological data based on a disease state or a biomarker feature and a quality score may include determining that the quality score exceeds a threshold acceptance value and determining the disease state or the biomarker of the patient physiological data based on the disease state or biomarker feature.

Issue Detector 208 may use such metadata to determine ambient or environmental conditions that existed during the measurement process that produced the patient physiological data. For example, metadata measured by an IMU (e.g., or an accelerometer) of the camera may include relative motion between the camera and a user's fingertip and the orientation of the camera (e.g., and thus the orientation of the mobile device housing the camera). In some embodiments, translational and rotational motion of the camera may be represented by one or more motion signatures, which may be represented by a waveform or plot of values. For example, translational motion may be a plot or table of time-dependent values of displacement of the camera relative to a fixed point in space. The plot or table may lead to a motion signature for the camera during a time span. Similarly, rotational motion may be one or more plots or tables of time-dependent values of pitch, yaw, and roll of the camera relative to a fixed axis. The plots or tables may lead to other types of motion signatures for the camera during a time span. Various features of the motion signatures may be analyzed. Such features may include frequency-of-motion (e.g., Fourier analysis of motion signatures in the frequency domain), shapes of waveforms or curves, and duration of such features (e.g., when they occurred relative to the time of data acquisition and for how long they occurred), just to name a few possible features. For example, a motion signature expressing displacement of the camera may include a feature that indicates that the camera was not resting on a stable surface (e.g., a tabletop). Such a feature may be a relatively low frequency (e.g., 5-10 Hz) component of the motion signature, which may be a result of the camera being hand-held during data acquisition. This type of motion may likely adversely affect the quality of data acquired during the time of this motion because the proximity of the fingertip to the camera may be difficult to hold constant with this type of motion. In another example, a motion signature expressing angular displacement, such as a relatively slow roll, of the camera may include a feature that also indicates that the camera was not resting on a stable surface. This type of motion, however, may not affect the quality of data acquired during the time of this motion because the proximity of the fingertip to the camera may nevertheless be held constant with this type of motion. Such dynamics of camera motion, as given in these and other examples, may be captured in motion signatures. Accordingly, analyzing these dynamics and how they affect motion of a fingertip or other tissue during data acquisition may allow for assessing the quality of the data.

In other embodiments, relative motion between the fingertip and the camera may be determined based, at least in part, on intensity measurements of pixel data of multiple image frames. For example, substantial changes of light intensity among image frames may indicate to Issue Detector 208 that relative motion occurred during capture of these image frames. In still other embodiments, relative motion between the fingertip and the camera may be determined based, at least in part, on motion signatures in combination with intensity measurements of pixel data of multiple image frames. In still other embodiments, relative motion between the fingertip and the camera may be determined to be zero if a signal from a capacitive touch sensor, which may be onboard the handheld device and relatively near or on the lens of the camera, indicates continuous contact between the fingertip and the camera during data acquisition.

If an issue is detected, then Issue Detector 208 may send a signal or message to Biomarker Detector UI 204, as indicated by arrow 220, to discard or prevent the further processing of particular samples of the collected frames of video/data. Moreover, Issue Detector 208 may send a signal or message to Biomarker Detector UI 204 including instructions for the Biomarker Detector UI to adjust in real-time a parameter of ambient conditions, the adjusting being based on the determination, by the Issue Detector, that the signal characteristic of the pseudo PPG signal does not meet a quality criterion. The ambient conditions may include relative motion between the camera and the user's finger (or other tissue) and the ambient light to which the sensor is exposed. Such adjustments in real-time may occur during the measurement process.

In particular, Issue Detector 208 may continuously or periodically look for issues that prevent production of high-quality signals. System 200 may include a detector, or process of detection, for each problematic issue, which, upon detection, may be provided as feedback to the user, via the UI of client application 202. For example, if a detector detects a problematic issue, the user may be alerted and Biomarker Detection module 210 may be reset.

As mentioned above, some examples of problematic issues may include a finger-off condition, motion/instability of the camera, motion/unstable ambient lighting condition, and phone orientation problem, just to name a few examples. In a particular implementation, a finger-off condition may be detected by gathering the last 500 milliseconds (ms) of video frames and analyzing the ratios of red to blue and green to identify whether the user's finger is correctly on the camera. A threshold for the ratio values may be dynamically selected based on the overall intensity in the collected frames to account for variables such as skin tone and camera settings. These thresholds may be identified empirically through collected fingertip video data where fingers are determined to be on or off at different intensities and camera settings. The image frame may also be segmented into quadrants (e.g., or other proportions), with ratios and thresholds being determined for each quadrant, with finger-off condition being identified if at least one quadrant's ratio is below a threshold. In another implementation, a finger-off condition may be detected by analyzing motion signatures of the camera, as described above.

In a particular implementation, a motion/unstable ambient lighting condition may be detected by gathering the last 500 ms of video frames and looking for the difference between minimum and maximum red pixel values. If the difference is more than a threshold value (e.g., 20 in a range of 0-255), it may be determined that too much motion has occurred or that the ambient lighting is too unstable. A phone orientation problem may occur if the user does not hold the phone relatively flat, thus affecting the amount of ambient light that reaches the camera. An on-board accelerator in the phone may be used to determine if the phone is flat, for example.

Assuming that no problematic issues, such as those described above, are detected, PPG Signal Generator 206 may generate a PPG signal/red channel, as indicated by arrow 222, for further analysis and evaluation by Biomarker Detection module 210.

In some embodiments, the services and functionality of system 200 may be combined with different ground truth data to generate measures of other health-related quantities and/or to provide greater insight into a user's health. For example, system 200 may be used to provide one or more of the following measurements if the appropriate ground truth is available: Sp02, involving use of a hypoxia tent to lower the subject's blood oxygen level and use of the Sp02 readings from a pulse oximeter; Blood glucose, involving the taking of blood glucose measurements via a finger stick and capturing data from a user before and after a meal; Hemoglobin A1C (HbA1c), involving taking a HbA1c measurement via a finger stick and lab analysis or point-of-care HbA1c analyzer; Heart rate variability, using an ECG device; Hemoglobin, using a hemoglobin measurement device; Respiration rate, by attaching a respiration rate band onto the user; and Arrhythmia, using an ECG device. Issue Detector 208, Environment Assessor 212, and Signal Quality Assessor 214 described above as applied to blood pressure and heart rate measurements may instead or also be used to make measurements of Sp02, blood glucose, heart rate variability, hemoglobin, respiration rate, and arrhythmia. Further, in some embodiments, the camera (image/video sensor) of the mobile device may be combined with other sensors on the device to collect additional data and signals that may be used to assist in evaluating a user's health or condition.

As discussed above, biomarkers, such as blood pressure, hbA1c, hypertension risk, and heart rate, for example, may be estimated based on biosensor data, such as a PPG. Optical biosensor data may be acquired from a smartphone-captured video of a person's finger using a system such as 200. For example, measurements of real-time blood pressure and heart rate data, or other biomarker, may be acquired via fingertip video obtained with a mobile device. In this context, for example, "real-time" refers to a situation where such biomarkers may be provided to a user while the user continues to be measured for the biomarkers, the latter measurements perhaps providing updated measurements. In an implementation, a user may use a smartphone, including a DMM, to measure their blood pressure and heart rate by placing their fingertip against the lens of the smartphone camera.

In some embodiments, a PPG signal may be acquired from a smartphone by averaging all pixels from the red channel of video of a fingertip from the smartphone. This process may produce a 1D (one-dimensional) time-series signal that mimics a PPG signal. However, this signal may generally be noisier than a signal acquired from a specially designed device like a pulse oximeter and may generally have a lower sampling rate. In one implementation, a region-of-interest (e.g., the middle 200×200 pixels) may be used. In another implementation, the frames of the smartphone video may be used to create the 1D time-series PPG signal using a deep learning model. Herein, a deep learning model refers to a neural network model that utilizes one or more of the following types of layers: convolutional, residual, recurrent, attentional, and transformer. For models operating on the smartphone video frames, there may be two different types of deep learning models used: a 2D model that operates independently on each individual frame, and a 3D model that operates on two or more frames at one time. In both cases, the model produces a time-series of embeddings that may be used to produce an output, which may be another embedding, a prediction of a pulse oximeter signal, a biomarker estimation, and so on.

Figure 3:
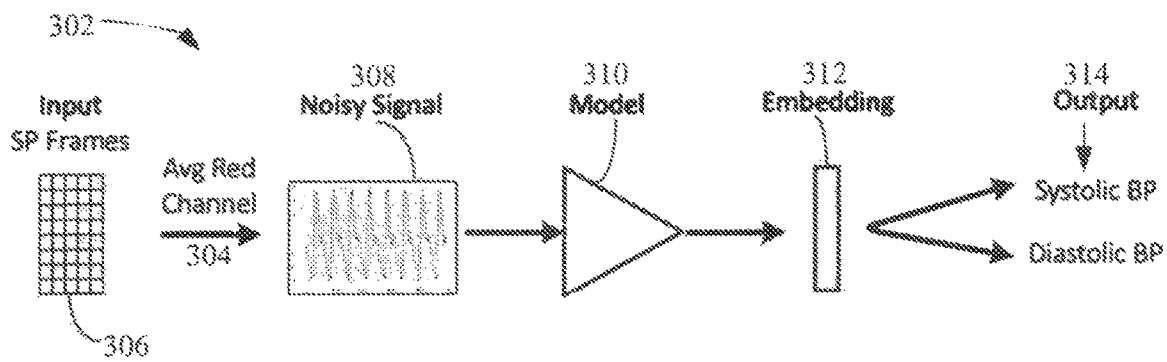
FIG. 3 illustrates a process that uses a baseline model incorporating an averaged red video channel to create a time-series signal that resembles a PPG signal, according to some embodiments.

In one type of deep learning model, a baseline may be produced by a baseline biomarker estimation system that involves passing the averaged red channel signal or time-series of video frames through a deep learning model to predict the biomarker. FIG. 3 illustrates a process 302 that uses this type of baseline model, wherein the averaged red channel 304 of input video frames 306 is used to create a 1D time-series noisy signal 308 that resembles a PPG signal. This signal may then be passed through a deep learning model 310 that uses embedding 312 to produce an output 314, which may be predicted biomarkers such as systolic and diastolic blood pressure.

Figure 4:
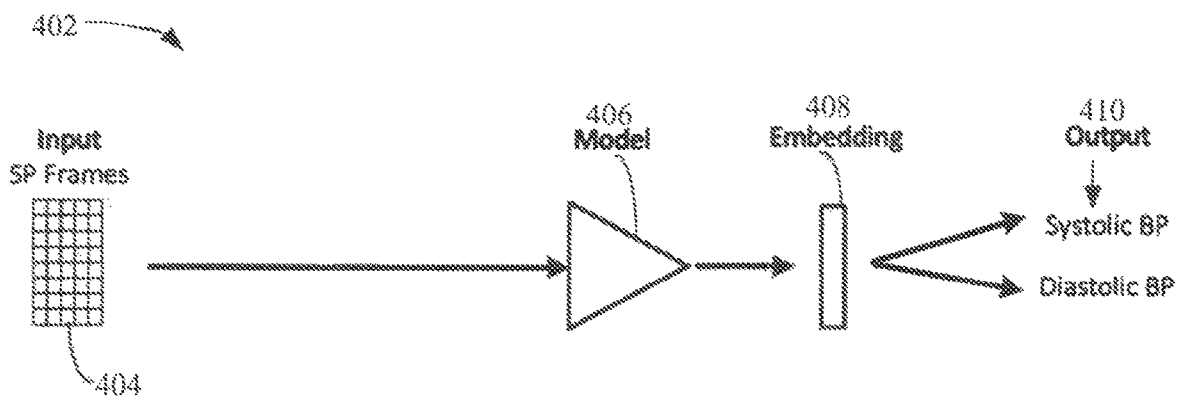
FIG. 4 illustrates a process that uses a baseline model incorporating a time-series of video frames that are passed directly to a deep learning model to predict a biomarker, according to some embodiments.

FIG. 4 illustrates another process that uses a different type of baseline model, wherein a time-series of video frames are passed directly through a deep learning model to predict the biomarker. Process 402 provides a time-series of video frames 404 directly to a deep learning model 406, which may use embedding 408 to produce an output 410, which may be predicted biomarkers such as systolic and diastolic blood pressure.

Figure 5:
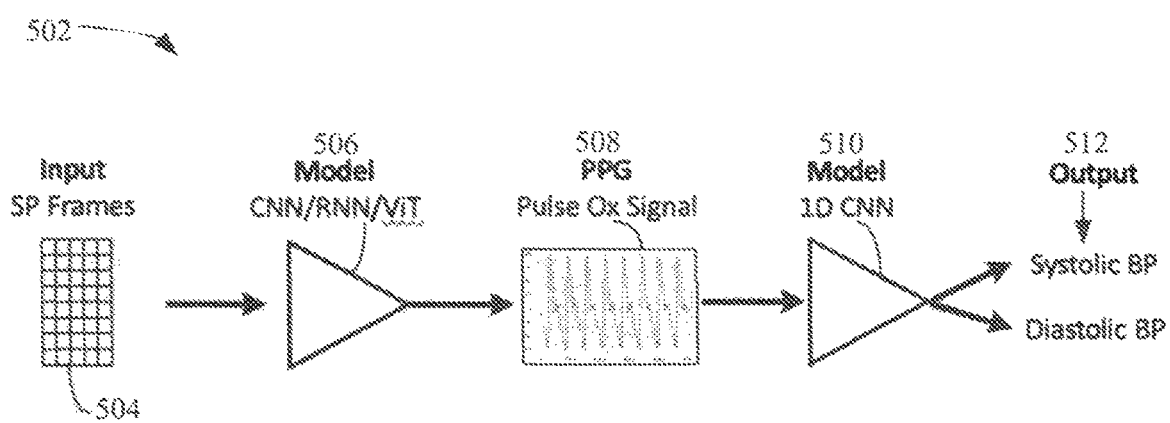
FIG. 5 illustrates a process that involves using raw smartphone video frames to predict a pulse oximeter signal that is subsequently used to estimate biomarkers such as blood pressure, according to some embodiments.

In some embodiments, a deep learning model may be trained to use smartphone data to predict a paired pulse oximeter signal. The input to the model may be the 1D time-series smartphone data, described above, from the averaging of the red channel or computed from the frames of the video. The predicted pulse oximeter signal may then be used as input to the deep learning model that will predict the biomarker. For example, FIG. 5 illustrates a process 502 that involves providing raw smartphone frames 504 to a deep learning model 506 to predict a pulse oximeter PPG signal 508, which may in turn be passed through a deep learning model 510 to produce an output 512 that may be predicted biomarkers such as systolic and diastolic blood pressure. In other embodiments, the averaged red channel smartphone signal and pulse oximeter signals may be passed into a model to predict a biomarker. The embeddings produced by the model may be passed into an adversarial discriminator to determine whether the sample was a smartphone or pulse oximeter signal. This helps to align the embedding spaces of both types of signals and can improve accuracy on the noisier of the two signals. Domain adaptation on the model embedding can be combined with other iterations described below, wherein the embedding produced by the biomarker estimation model is passed into a discriminator to predict the domain of the input signal.

Figure 6:
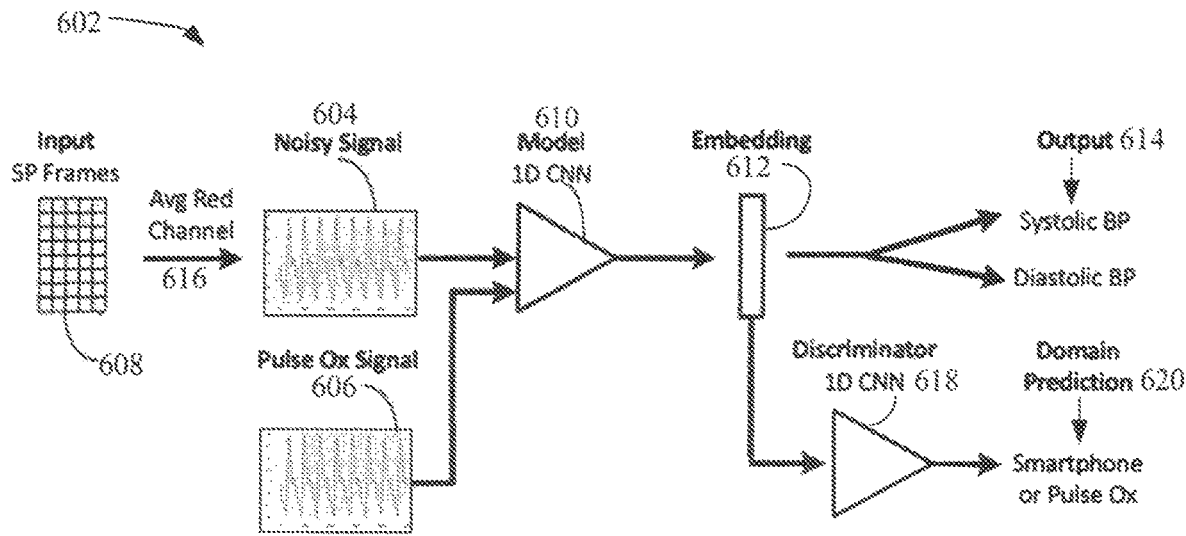
FIG. 6 illustrates a process where smartphone and pulse oximeter data are both used for training a deep learning model, and embeddings produced by the model are passed through a discriminator model to predict the domain of an input signal, according to some embodiments.

FIG. 6 illustrates a process 602 where smartphone and pulse oximeter data are both used in training. Embeddings produced by the model are passed through a discriminator model to predict the domain of the input signal. Process 602 produces noisy PPG signal 604 and pulse oximeter PPG signal 606 from averaged red channel video frames 608. Both PPG signals are provided to a deep learning model 610, which may use embedding 612 to produce an output 614, which may be predicted biomarkers such as systolic and diastolic blood pressure. In some embodiments, the averaged red channel 616 is passed through deep learning model 610 to produce a clean signal. A discriminator model 618 uses domain prediction 620 to determine whether this clean signal is from a smartphone or pulse oximeter 606.

Figure 7:
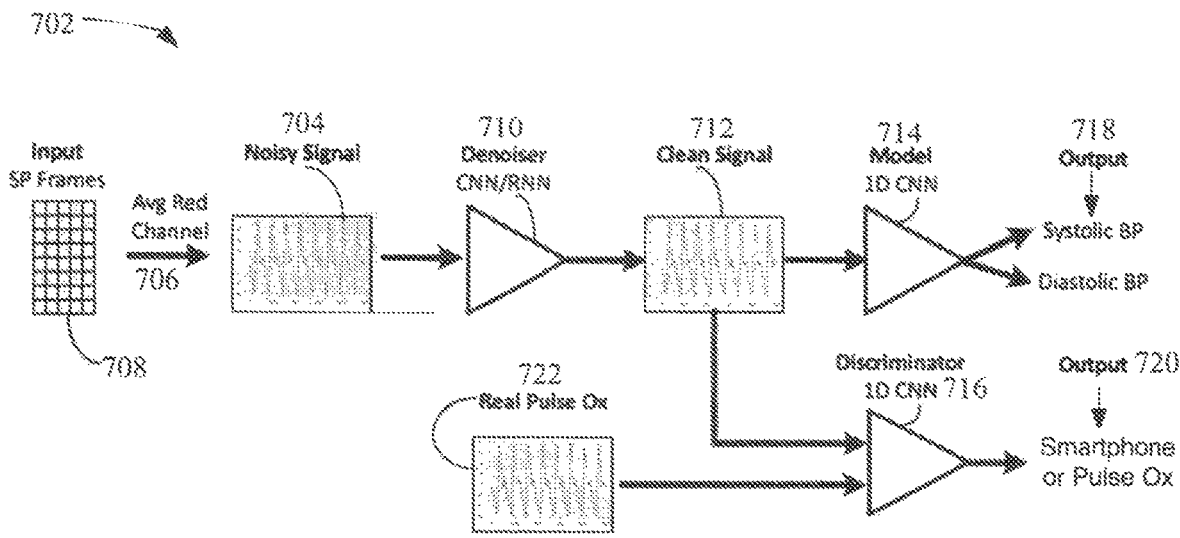
FIG. 7 illustrates domain adaptation by analyzing a denoised signal using the averaged red channel of a video signal as input, according to some embodiments.

FIG. 7 illustrates a process 702 of domain adaptation by analyzing a denoised signal using the averaged red channel as input. Process 702 produces a noisy PPG signal 704 from the averaged red channel 706 of video frames 708. The PPG signal is provided to a denoiser 710, which may comprise a deep learning model, for example. Output from denoiser 710 is clean PPG signal 712, which may be provided to another deep learning model 714 and a discriminator 716. Deep learning model 714 may produce an output 718, which may be predicted biomarkers such as systolic and diastolic blood pressure. Discriminator 716 may produce an output 720 that indicates whether this output is from a smartphone or a pulse oximeter 722.

Figure 8:
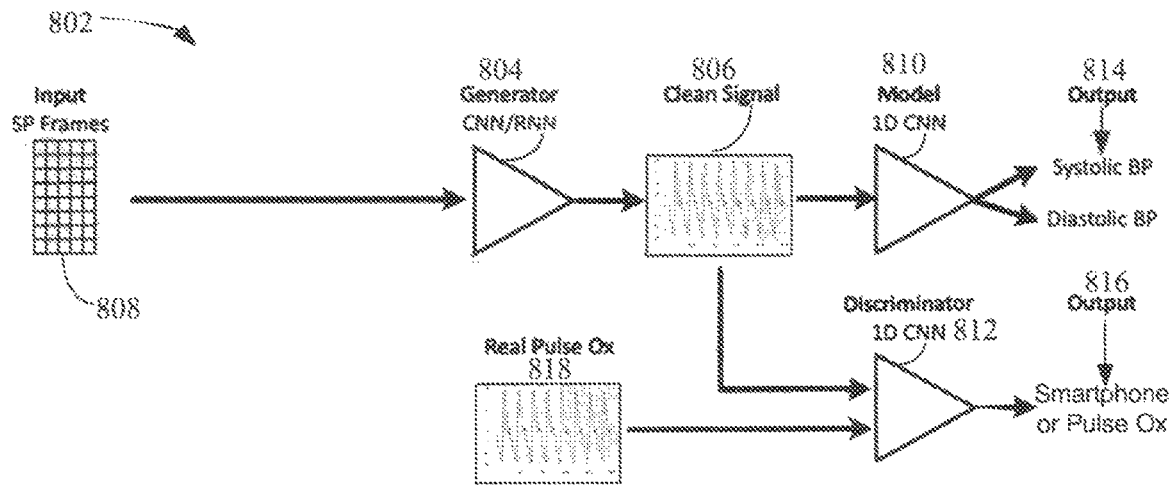
FIG. 8 illustrates domain adaptation by analyzing a denoised signal using a smartphone-captured video as input, according to some embodiments.

FIG. 8 illustrates a process 802, which is the same as process 702 except that instead of using an averaged red channel signal (e.g., 706), the video frames of the smartphone can be directly used instead. Using a deep learning model 804, process 802 produces a clean PPG signal 806 directly from video frames 808. Clean PPG signal 806 may be provided to another deep learning model 810 and a discriminator 812. Deep learning model 810 may produce an output 814, which may be predicted biomarkers such as systolic and diastolic blood pressure. Discriminator 812 may produce an output 816 that indicates whether this output is from a smartphone or a pulse oximeter 818.

Figure 9:
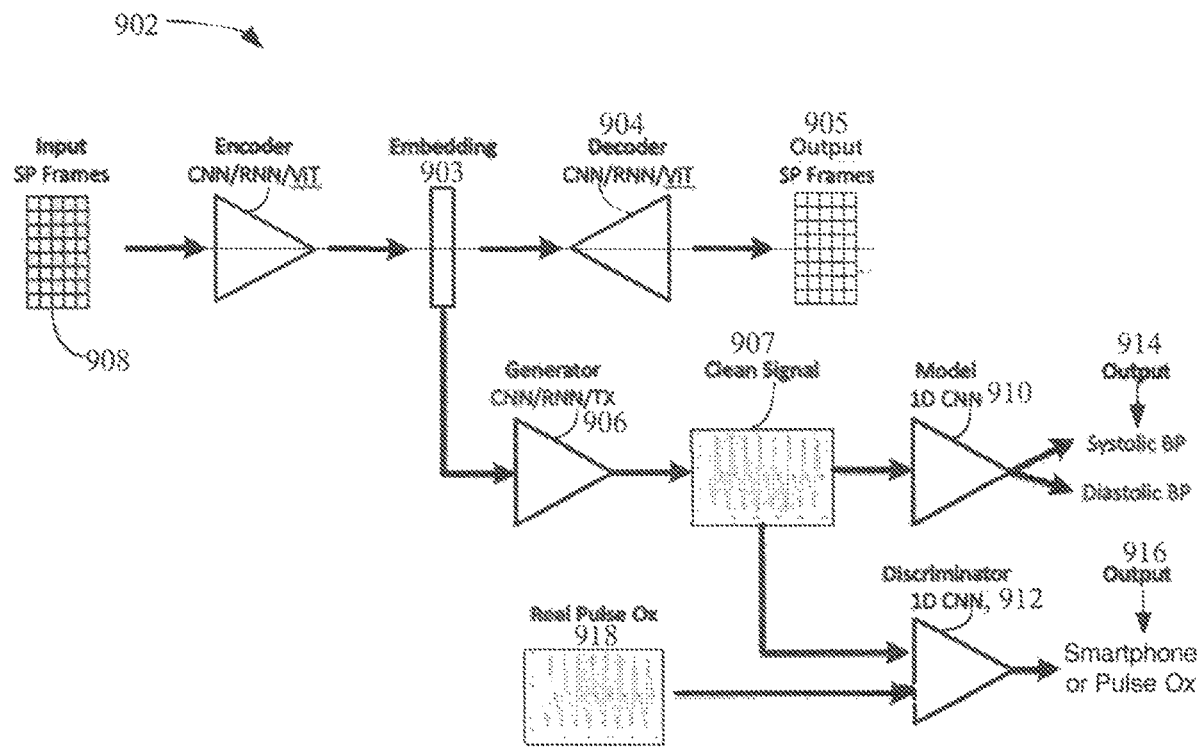
FIG. 9 illustrates domain adaptation by analyzing a denoised signal using an autoencoder embedding as input, according to some embodiments.

FIG. 9 illustrates a process 902, which is the same as process 802, except it utilizes an autoencoder setup that creates embeddings 903 which are used as input to a generator 904. These embeddings are created outside of the end-to-end system and can provide a more generalizable representation 905. For example, using a deep learning model 906, process 902 produces a clean PPG signal 907 based on video frames 908. Clean PPG signal 906 may be provided to another deep learning model 910 and a discriminator 912. Deep learning model 910 may produce an output 914, which may be predicted biomarkers such as systolic and diastolic blood pressure. Discriminator 912 may produce an output 916 that indicates whether this output is from a smartphone or a pulse oximeter 918.

In some embodiments, additional information such as demographics or features may be concatenated to each frame of data analyzed by the kernel of the convolution in an early fusion scheme. By providing this data to the model at the convolutional stage, it is able to utilize the information to better analyze the signal.

In some embodiments, the deep learning model may be trained in a multi-task learning scheme, where the model predicts both the biomarker of interest and additional other features. Training using this scheme can allow the model to create more generalizable features. As an example, heart rate may be calculated for a given PPG signal using a deterministic FFT-based algorithm. The deep learning model would then be trained to predict both the biomarker and the heart rate.

In some embodiments, the deep learning model may utilize a temporary prediction of a biomarker in the subsequent prediction of a different but related biomarker. For example, diastolic and systolic blood pressure are related quantities. The deep learning model may predict temporary values for systolic and diastolic, both of which would be fed back to the deep learning model for the final systolic and diastolic prediction.

In some embodiments, the prediction from multiple different models may be aggregated for the final prediction. For example, the prediction from a network with convolutional kernel size of 3 may be averaged with the prediction from a network with convolutional kernel size of 5. The averaged prediction would be used as the final prediction.

Figure 10:
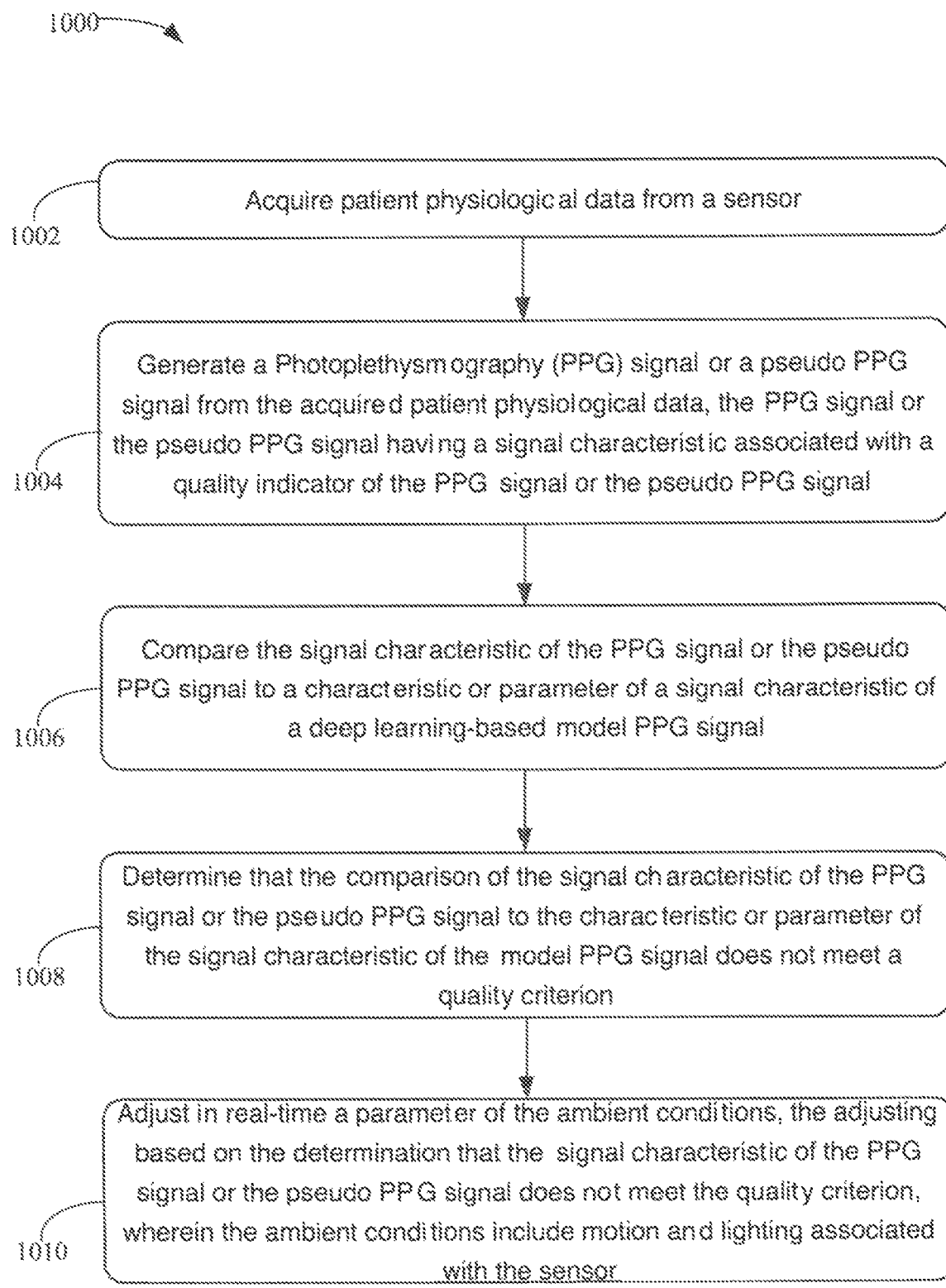
FIG. 10 is a flow diagram of a process for addressing signal quality of a PPG signal, according to some embodiments.

FIG. 10 is a flow diagram of a process 1000 for addressing signal quality of a PPG signal, according to some embodiments. For example, a computer processing system (e.g., a processor) may perform process 1000. At 1002, the processor may acquire patient physiological data from a sensor. For example, client application 202 may use Biomarker Detector UI 204 operate a camera of a mobile device. At 1004, the processor may generate a PPG signal or a pseudo PPG signal from the acquired patient physiological data. The pseudo PPG signal may have a signal characteristic associated with a quality indicator of the pseudo PPG signal. In other words, a feature of the pseudo PPG signal, such as the detailed shape of a waveform or pulse, for example, may allow for quantifying or characterizing the quality of the pseudo PPG signal. The feature may also allow for determining the circumstances (e.g., ambient conditions) that existed during acquisition of the patient physiological data.

At 1006, the processor may compare the signal characteristic of the pseudo PPG signal to a characteristic or parameter of a signal characteristic of a deep learning-based model PPG signal. For example, after being provided to Biomarker detection module 210, the signal characteristic of the pseudo PPG signal may be compared to a characteristic or parameter of an analogous signal characteristic of a deep learning-based model PPG signal. At 1008, the processor may determine that the comparison of the signal characteristic of the pseudo PPG signal to the characteristic or parameter of the signal characteristic of the model PPG signal does not meet a quality criterion. At 1010, the processor may adjust in real-time a parameter of the ambient conditions. The adjusting may be based on the determination that the signal characteristic of the pseudo PPG signal does not meet the quality criterion. The ambient conditions may include motion and lighting associated with the sensor.

Figure 11:
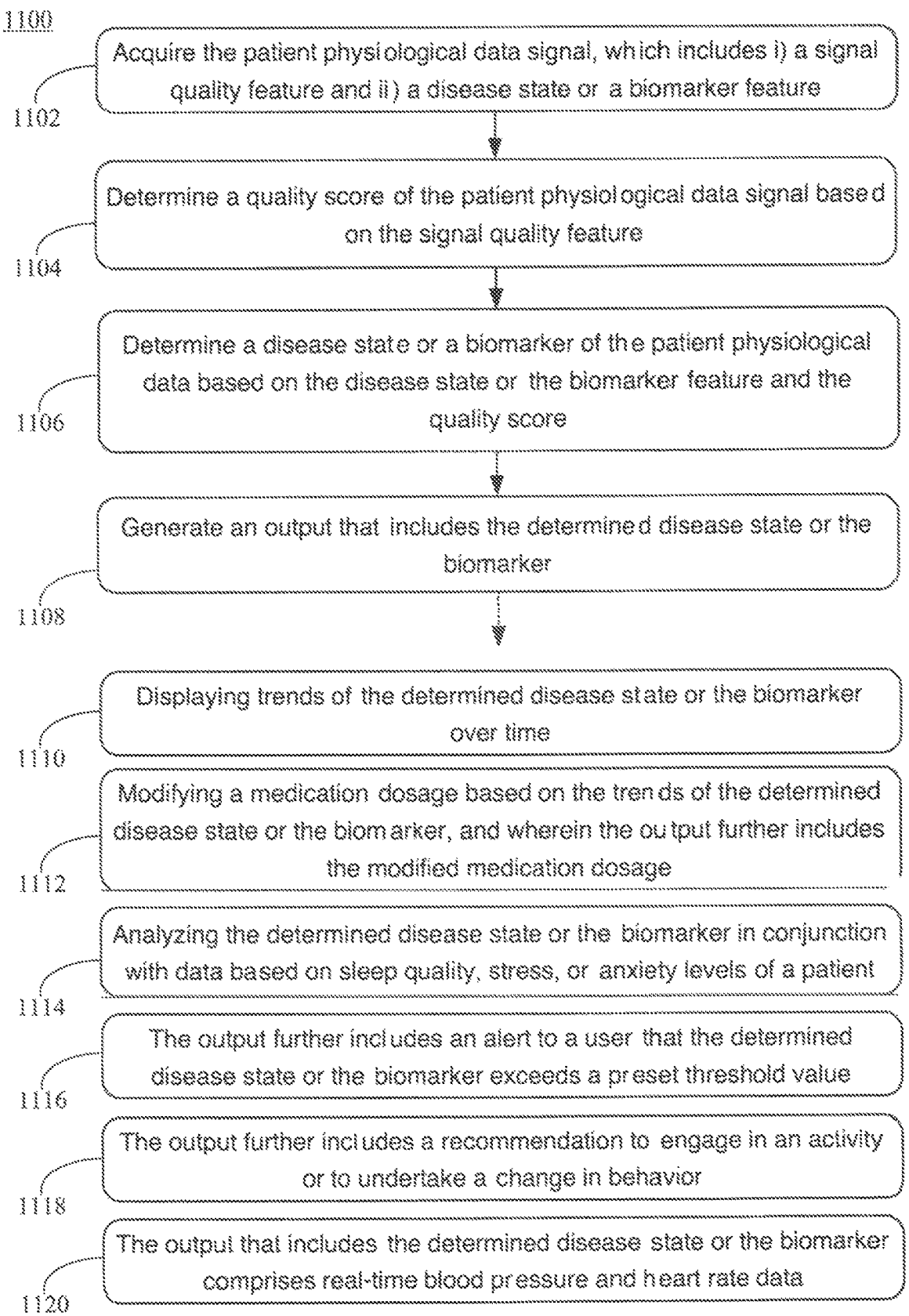
FIG. 11 is a flow diagram of a process for determining signal quality of a PPG signal and determining a disease state or biomarker based on the PPG signal, according to some embodiments.

FIG. 11 is a flow diagram of a process 1100 for determining signal quality of a PPG signal and determining a disease state or biomarker based on the PPG signal, according to some embodiments. For example, a computer processing system (e.g., a processor) may perform process 1100. At 1102, the processor may acquire the patient physiological data signal, which may include a signal quality feature and a disease state or a biomarker feature. At 1104, the processor may determine a quality score of the patient physiological data signal based on the signal quality feature. At 1106, the processor may determine a disease state or a biomarker of the patient physiological data based on the disease state or the biomarker feature and the quality score. At 1108, the processor may generate an output that includes the determined disease state or the biomarker. In some implementations the output may further include displaying trends of the determined disease state or the biomarker over time.

In some implementations, an application (e.g., 202) may modify a medication dosage based on the trends of the determined disease state or the biomarker. The application may then display to a user the modified medication dosage. In some cases, the application may analyze the determined disease state or the biomarker in conjunction with data based on sleep quality, stress, or anxiety levels of a patient. The display or other portion of a UI may further include an alert to a user that the determined disease state or the biomarker exceeds a preset threshold value. The display may also include a recommendation to engage in an activity or to undertake a change in behavior, and the real-time blood pressure and heart rate data.

Figure 12:
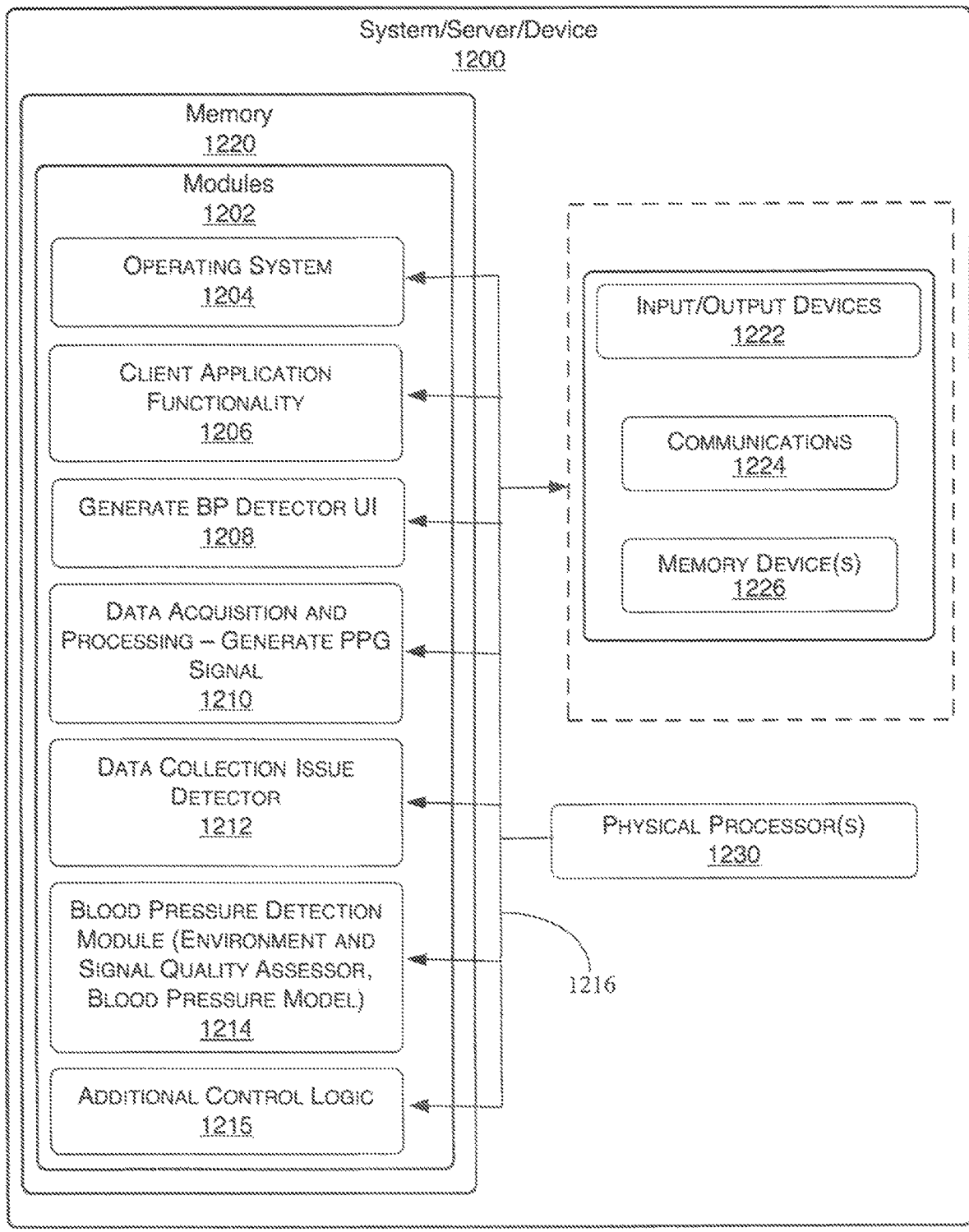
FIG. 12 illustrates elements or components of a computer device or system configured to implement a method, process, function, or operation of some embodiments described herein.

FIG. 12 illustrates elements or components of a computer device or system configured to implement a method, process, function, or operation of some embodiments of a system (e.g., 200) and methods described herein. As noted, in some embodiments, the system and methods may be implemented in the form of an apparatus that includes a processing element and a set of executable instructions. The executable instructions may be part of a software application and arranged into a software architecture.

In general, an embodiment may be implemented using a set of software instructions that are designed to be executed by a suitably programmed processing element (such as a GPU, CPU, microprocessor, processor, controller, computing device, etc.). In a complex application or system such instructions are typically arranged into "modules" with each such module typically performing a specific task, process, function, or operation. The entire set of modules may be controlled or coordinated in their operation by an operating system (OS) or other form of organizational platform.

Each application module or sub-module may correspond to a particular function, method, process, or operation that is implemented by execution of the instructions contained in the module or sub-module. Such function, method, process, or operation may include those used to implement one or more aspects, techniques, components, capabilities, steps, or stages of the described system and methods. In some embodiments, a subset of the computer-executable instructions contained in one module may be implemented by a processor in a first apparatus and a second and different subset of the instructions may be implemented by a processor in a second and different apparatus. This may happen, for example, where a process or function is implemented by steps that occur in both a client device and a remote server.

The application modules and/or sub-modules may include any suitable computer executable code or set of instructions (e.g., as would be executed by a suitably programmed processor, microprocessor, or CPU), such as computer-executable code corresponding to a programming language. For example, programming language source code may be compiled into computer-executable code. Alternatively, or in addition, the programming language may be an interpreted programming language such as a scripting language.

The modules may contain one or more sets of instructions for performing a method or function described with reference to the figures. These modules may include those illustrated but may also include a greater number or fewer number than those illustrated. As mentioned, each module may contain a set of computer-executable instructions. The set of instructions may be executed by a programmed processor contained in a server, client device, network element, system, platform, or other component.

A module may contain computer-executable instructions that are executed by a processor contained in more than one of a server, client device, network element, system, platform or other component. Thus, in some embodiments, a plurality of electronic processors, with each being part of a separate device, server, platform, or system may be responsible for executing all or a portion of the instructions contained in a specific module. Thus, although FIG. 12 illustrates a set of modules which taken together perform multiple functions or operations, these functions or operations may be performed by different devices or system elements, with certain of the modules (or instructions contained in those modules) being associated with those devices or system elements.

As illustrated in FIG. 12, system 1200 may represent a server or other form of computing or data processing system, platform, or device. Modules 1202 each contain a set of computer executable instructions, where when the set of instructions is executed by a suitable electronic processor or processors (such as that indicated in the figure by "Physical Processor(s) 1230"), system (or server, platform, or device) 1200 operates to perform a specific process, operation, function, or method. Modules 1202 are stored in a memory 1220, which typically includes an Operating System module 1204 that contains instructions used (among other functions) to access and control the execution of the instructions contained in other modules. The modules 1202 stored in memory 1220 are accessed for purposes of transferring data and executing instructions by use of a "bus" or communications line 1216, which also serves to permit processor(s) 1230 to communicate with the modules for purposes of accessing and executing a set of instructions. Bus or communications line 1216 also permits processor(s) 1230 to interact with other elements of system 1200, such as input or output devices 1222, communications elements 1224 for exchanging data and information with devices external to system 1200, and additional memory devices 1226.

For example, Module 1206 may contain computer-executable instructions which when executed by a programmed processor cause the processor or a device containing the processor to perform the functions of the client application to enable the collection and processing of the acquired data either on the device or (as an example) to navigate to a server, upload the video or other data to the server, receive the output(s) of the blood pressure model from the server, and present the output(s) to the user (in the form of a measure, graph, chart, range etc.). Module 1208 may contain computer-executable instructions which when executed by a programmed processor cause the processor or a device containing the processor to generate a blood pressure detector user interface for presentation to a user. The interface may provide the user with tools and instructions for collecting the video data using their device (such as a smartphone).

The functionality for data acquisition, data processing, issue detection, and the determination of blood pressure or another health-related quantity may be provided to a user in one or more formats. These include an SDK that developers can use to perform one or more of the functions (such as data collection, initial data processing, issue detection, running the blood pressure model) in their own applications. In another embodiment, a downloaded client application is provided that is capable of performing one or more of the functions directly to an end user. In another embodiment, certain functions of the client application may be replaced by services accessible through an account on a SaaS platform.

In any of these embodiments, the trained models may reside as services on a remote server or platform so that the models can be updated and continually trained and improved as new data becomes available. This arrangement may allow anonymized data collected from multiple users to be made available to other developers and model builders for use in determining other health-related quantities and for determining correlations between medical conditions, health, and the quantities. In any of these embodiments, the interface may be provided through the web, mobile, or desktop, as long as there is an attached video camera.

Module 1210 may contain computer-executable instructions which when executed by a programmed processor cause the processor or a device containing the processor to acquire the video data and subject it to processing (image and/or signal processing) to extract the red channel of the video, and to treat this signal as a pseudo-PPG signal. Module 1212 may contain computer executable instructions which when executed by a programmed processor cause the processor or a device containing the processor to monitor for issues or concerns that may occur during the video/data collection and to assist in determining if the collected video/data is useable for generating the pseudo-PPG signal. Module 1214 may contain computer-executable instructions which when executed by a programmed processor cause the processor or a device containing the processor to perform functions used to generate a blood pressure measure from the acquired video in cases where the Issue Detector has not prevented further processing of the video frames. As illustrated in the figure, this may include consideration of environmental conditions and signal quality prior to inputting the pseudo-PPG signal (e.g., the red channel of the video) into a trained blood pressure model. Module 1215 may contain computer-executable instructions which when executed by a programmed processor cause the processor or a device containing the processor to execute additional control logic for managing the decision processes involved in obtaining device or camera parameters, setting parameters of the video/data collection process, and controlling the video/data processing flow, configuring a response to the determined blood pressure measures, etc.

In some embodiments, certain of the functionality and services provided by the system and methods described herein may be made available to multiple users by accessing an account maintained by a server or service platform. Such a server or service platform may be termed a form of Software-as-a-Service (SaaS).

It should be understood that the embodiments described above can be implemented in the form of control logic using computer software in a modular or integrated manner. Based on the disclosure and teachings provided herein, a person of ordinary skill in the art will know and appreciate other ways and/or methods to implement the embodiments using hardware and a combination of hardware and software.

In some embodiments, certain of the methods, models or functions described herein may be embodied in the form of a trained neural network, where the network is implemented by the execution of a set of computer-executable instructions or representation of a data structure. The instructions may be stored in (or on) a non-transitory computer-readable medium and executed by a programmed processor or processing element. The set of instructions may be conveyed to a user through a transfer of instructions or an application that executes a set of instructions (such as over a network, e.g., the Internet). The set of instructions or an application may be utilized by an end-user through access to a SaaS platform or a service provided through such a platform. A trained neural network, trained machine learning model, or other form of decision or classification process may be used to implement one or more of the methods, functions, processes, or operations described herein. Note that a neural network or deep learning model may be characterized in the form of a data structure in which are stored data representing a set of layers containing nodes, and connections between nodes in different layers are created (or formed) that operate on an input to provide a decision or value as an output.

In general terms, a neural network may be viewed as a system of interconnected artificial "neurons" that exchange messages between each other. The connections have numeric weights that are "tuned" during a training process, so that a properly trained network will respond correctly when presented with an image or pattern to recognize (for example). In this characterization, the network consists of multiple layers of feature-detecting "neurons"; each layer has neurons that respond to different combinations of inputs from the previous layers. Training of a network is performed using a "labeled" dataset of inputs in a wide assortment of representative input patterns that are associated with their intended output response. Training uses general-purpose methods to iteratively determine the weights for intermediate and final feature neurons. In terms of a computational model, each neuron calculates the dot product of inputs and weights, adds the bias, and applies a non-linear trigger or activation function (for example, using a sigmoid response function).

Machine learning (ML) is being used more and more to enable the analysis of data and assist in making decisions in multiple industries. In order to benefit from using machine learning, a machine learning algorithm is applied to a set of training data and labels to generate a "model" which represents what the application of the algorithm has "learned" from the training data. Each element (or example, in the form of one or more parameters, variables, characteristics or "features") of the set of training data is associated with a label or annotation that defines how the element should be classified by the trained model. A machine learning model is a set of layers of connected neurons that operate to make a decision (such as a classification) regarding a sample of input data. When trained (i.e., the weights connecting neurons have converged and become stable or within an acceptable amount of variation), the model will operate on a new element of input data to generate the correct label or classification as an output.

An embodiment, which is provided as a particular example and is not intended to exclude other suitable methods, includes a methodology for training a biomarker estimation deep learning model, which may be trained on a large bank of biosignals (e.g., collected from public and private datasets). This may include PPG, ECG, seismocardiogram (SCG), ballistocardiogram (BCG), Electroencephalogram (EEG), and more. The output of the model may be a series of embeddings that are utilized to predict some downstream task.

The training may utilize both unsupervised and semi-supervised learning. For unsupervised, portions of the signal may be removed from the input sequence, and the model may be instructed to predict the missing portion of embeddings. In semi-supervised, certain characteristics of the signal may be calculated (such as heart rate from the PPG signal), for which the model will attempt to predict these portions. In another iteration of semi-supervised, certain characteristics about samples that are similar will be calculated (e.g., from the same person, have the same heart rate, etc.) and the model will be tasked with creating an embedding that is similar for these samples with the same characteristics.

The embeddings created by the model may then be used for biomarker estimation. A deep learning model may operate on the embeddings created by the large pre-trained model to predict the biomarker, which may be systolic BP and diastolic BP, for example.

For the large pretrained model, one may quantize the different values of the input signal. For example, for a signal that can take values of 0 to 1, one may create 1 million equally spaced states, where each value of the signal is rounded to the nearest state.

As discussed above, there may be multiple sources of time-synchronized sensor data collected at one time. For example, sources may include the pulse oximeter, IMU, ECG, or the smartphone optical and motion signals. These signals may be combined as separate channels of the input signal (e.g., channel 0=PPG, channel 1=accelerometer X, channel 2=accelerometer Y). The deep learning model would then operate on this multi-channel signal.

The deep learning model may be used to predict not only the biomarker of interest, but also additional features about the signal. For example, heart rate may be calculated from the PPG signal. The deep learning model would be instructed to predict both heart rate and the biomarker of interest. The prediction of these additional features can improve the performance of the biomarker prediction.

One such example is the prediction of pulse transit time (PTT). Using an IMU signal (motion) and optical signal, the time interval from when the aortic opening is sensed by the IMU and a landmark point in the optical signal (e.g., peak, valley, beginning of rise to systolic peak) may be measured. This time interval is PTT, which may be predicted by a model that contains both IMU and optical data. One may train different machine learning models for different demographics. For example, one may train a model for individuals of ages 0-40, 40-60, and 60+. During inference, one would use the model that matches the individual's demographics.

The data collected from the ear and toe pulse oximeters may be used to calculate the PTT. By using a landmark point in both signals (e.g., peak, valley, location of rise to systolic peak, etc.), the time interval between the landmark point in the ear and toe signals is calculated. Next, a deep learning model running on either just the optical fingertip signal or optical fingertip and IMU data may be used to predict that PTT value.

An embodiment, which is provided as a particular example and is not intended to exclude other suitable methods, includes a methodology for collecting training data for a model or models. A data collection process may include, for example, a data collection person or persons. They first guide a subject through a relaxation period, such as about five minutes, which may allow for stabilizing the subject's blood pressure. Then they may take blood pressure readings (discarding the first) and alternative blood pressure readings and fingertip videos on a variety of smartphones. Throughout this process, the subject may be connected to a pulse oximeter device to capture ground truth PPG. They also may take demographic information that may affect the reading, including age, height, weight, biological sex, hand size, and skin tone. To ensure accuracy of a BP (or other biomarker) reading, BP may be measured via auscultation and a digital stethoscope may be used along with a webcam. The webcam video may be spliced with stethoscope audio. A data collection application may record fingertip videos. This application may record fingertip video with frame-by-frame metadata that includes the current camera settings for each frame. To align the PPG reading and a smartphone fingertip reading, a breadboard that has a button hooked up to an LED (e.g., a red LED) and to the pulse oximeter may be used. The button activates the LED and sends a signal to the PPG device to start recording. The smartphone is held up to the LED and the smartphone and PPG signals may be aligned based on that light. The data collection process may be mobile to enable capture of training data from a greater diversity of subjects by going to them on-site rather than them having to come to a specific location. Once data is collected, it may be uploaded into cloud storage. Processing the data may begin once it's uploaded, automatically syncing the PPG and smartphone fingertip reading (by looking for a spike in the red), clipping the smartphone and PPG signals to just the relevant portions with the fingertip on the camera (by looking for ratio of red to blue and green), fine-tuning the alignment of the PPG and smartphone signal, scoring the smartphone signals, and producing plots that can be analyzed. This data can be used to train the model(s). In addition to preparing data and producing plots, a database may also be produced of individual pulses that include signal quality score info and demographic data that we can use to debug a model quickly. The system may potentially use the demographic data as input into the BP model for greater accuracy as well, and for segmenting users to provide more accurate BP values.

In some embodiments, the system or services described herein may be implemented as microservices, processes, workflows or functions performed in response to the submission of a set of input data. The microservices, processes, workflows or functions may be performed by a server, data processing element, platform, or system. In some embodiments, the data analysis and other services may be provided by a service platform located "in the cloud". In such embodiments, the platform may be accessible through APIs and SDKs. The functions, processes and capabilities described herein and with reference to one or more of the figures may be provided as microservices within the platform. The interfaces to the microservices may be defined by REST and GraphQL endpoints. An administrative console may allow users or an administrator to securely access the underlying request and response data, manage accounts and access, and in some cases, modify the processing workflow or configuration.

Note that although some embodiments described herein are directed to a multi-tenant or SaaS architecture that may be used for the delivery of business-related or other applications and services to multiple accounts/users, such an architecture may also be used to deliver other types of data processing services and provide access to other applications. For example, such an architecture may be used to provide one or more of the processes, functions, and operations described herein. Although in some embodiments, a platform or system of the type illustrated in the figures may be operated by a 3rd party provider to provide a specific set of services or applications, in other embodiments, the platform may be operated by a provider and a different entity may provide the applications or services for users through the platform.

Figure 13:
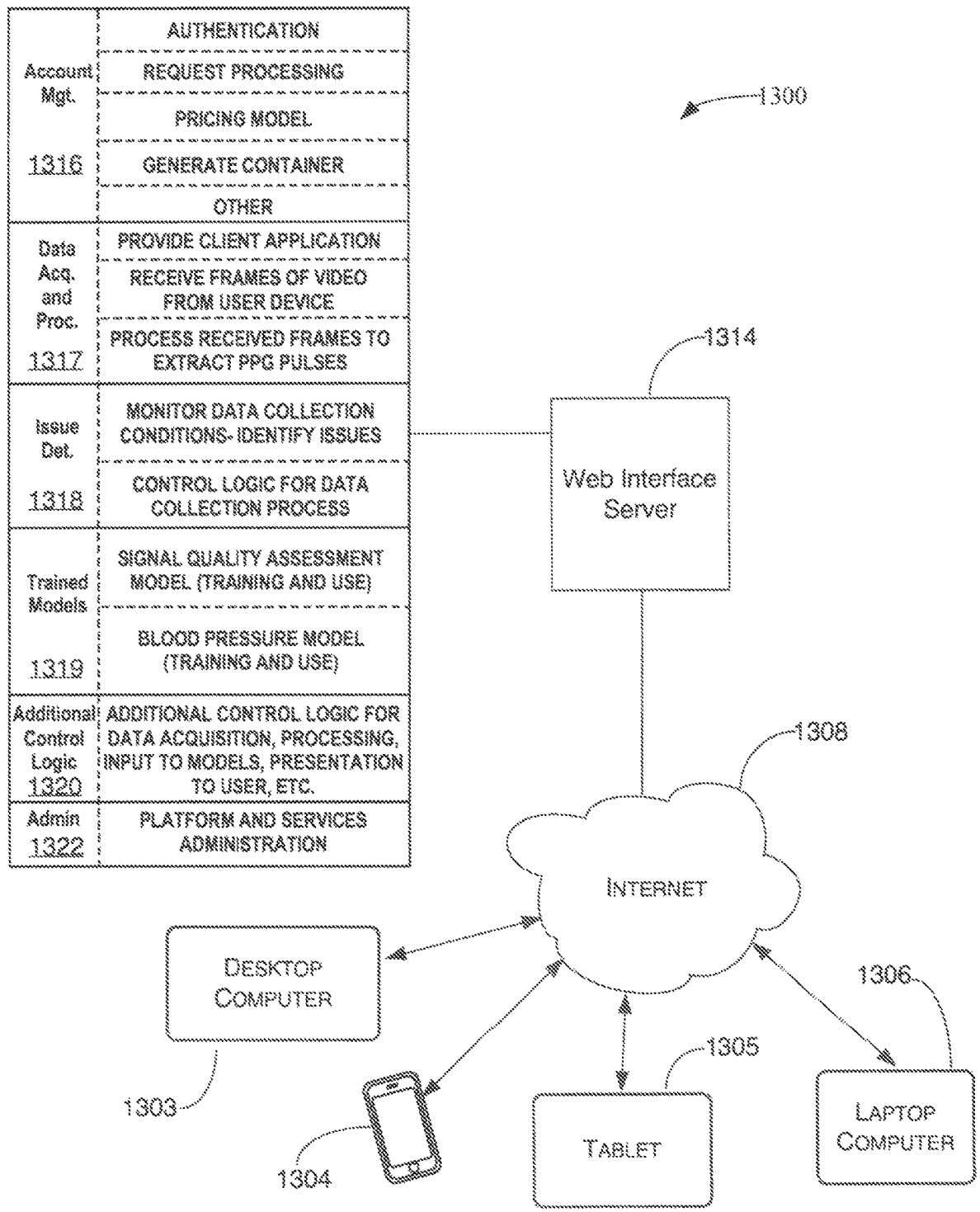
FIG. 13 illustrates a Software-as-a-Service (SaaS) system in which some embodiments described herein may be implemented.

FIG. 13 illustrates an SaaS system 1300 in which an embodiment may be implemented or through which an embodiment of the services described herein may be accessed. In accordance with the advantages of an application service provider (ASP) hosted business service system (such as a multi-tenant data processing platform), users of the services described herein may comprise individuals, businesses, stores, organizations, etc. A user may access the services using any suitable client, including but not limited to desktop computers, laptop computers, tablet computers, scanners, smartphones, etc. In general, any client device having access to the Internet may be used to provide data to the platform for processing and evaluation. A user interfaces with the service platform across the Internet 1308 or another suitable communications network or combination of networks. Examples of suitable client devices include desktop computers 1303, smartphones 1304, tablet computers 1305, or laptop computers 1306.

System 1300, which may be hosted by a third party, may include a set of data analysis and other services to assist in acquiring and processing video data, and generating a measure or measures of one or more health-related quantities, and a web interface server 1314. The services may include one or more functions or operations for the processing of acquired video or other data to enable the generation of a measure of blood pressure or other health-related quantity. As examples, in some embodiments, the set of functions, operations or services made available through the platform or system 1300 may include Account Management services 1316, which may implement a process or service to authenticate a user wishing to submit an example of video data and from that determine a measure of a health-related quantity, or which may implement a process or service to generate a container or instantiation of the data processing and analysis services for that user. System 1300 may also include Initial Data Acquisition and Processing services 1317, which may implement a process or service to provide a client-side application to a user for installation on their device, may implement a process or service to receive a set of frames of video data from the user device; or may implement a process or service to process each frame to extract a red or pseudo-PPG channel (the PPG Signal Generator)

System 1300 may also include Identify/Detect Video Collection Issues of Possible Concern services 1318, which may implement a process or service to monitor and detect one or more situations or events that might indicate the video data acquired during that situation or event is not reliable or accurate, or may implement a process or service to execute logic to control the collection or processing of the video frames based on the presence or absence of such a situation or event. System 1300 may also include Determine Blood Pressure Measure(s) and/or Other Health-Related Quantities services 1319, which may implement a process or service to assess environmental factors and signal quality factors (in one embodiment using a trained signal quality assessment model), and if those are acceptable, to provide the generated (extracted) PPG signal to a trained model. Determine Blood Pressure Measure(s) and/or Other Health-Related Quantities services 1319 may also implement a trained model that operates to receive the generated PPG signal extracted from the video frames and in response to generate a measure or measures of one or more health related quantities, such as blood pressure.

System 1300 may also include Control Logic services 1320, which may implement a process or service to implement other needed control logic to control the acquisition, processing, and use of the trained model(s), may implement a process or service to implement other logic for delivering and presenting the output of the trained blood pressure model to a user, including trend data and/or other forms of analysis of blood pressure measures, or may implement a process or service to implement logic to process data from other sensors and/or to process such data to generate other forms of signals for input to a trained model. System 1300 may also include administrative services 1322, which may implement a process or services to provide platform and services administration, such as, for example, enabling the provider of the services and/or the platform to administer and configure the processes and services provided to users.

The platform or system illustrated in FIG. 13 may be hosted on a distributed computing system made up of at least one, but likely multiple, "servers." A server is a physical computer dedicated to providing data storage and an execution environment for one or more software applications or services intended to serve the needs of the users of other computers that are in data communication with the server, for instance via a public network such as the Internet. The server, and the services it provides, may be referred to as the "host" and the remote computers, and the software applications running on the remote computers being served may be referred to as "clients." Depending on the computing service(s) that a server offers it could be referred to as a database server, data storage server, file server, mail server, print server, web server, etc. A web server is most often a combination of hardware and the software that helps deliver content, commonly by hosting a website, to client web browsers that access the web server via the Internet.

Figure 14:
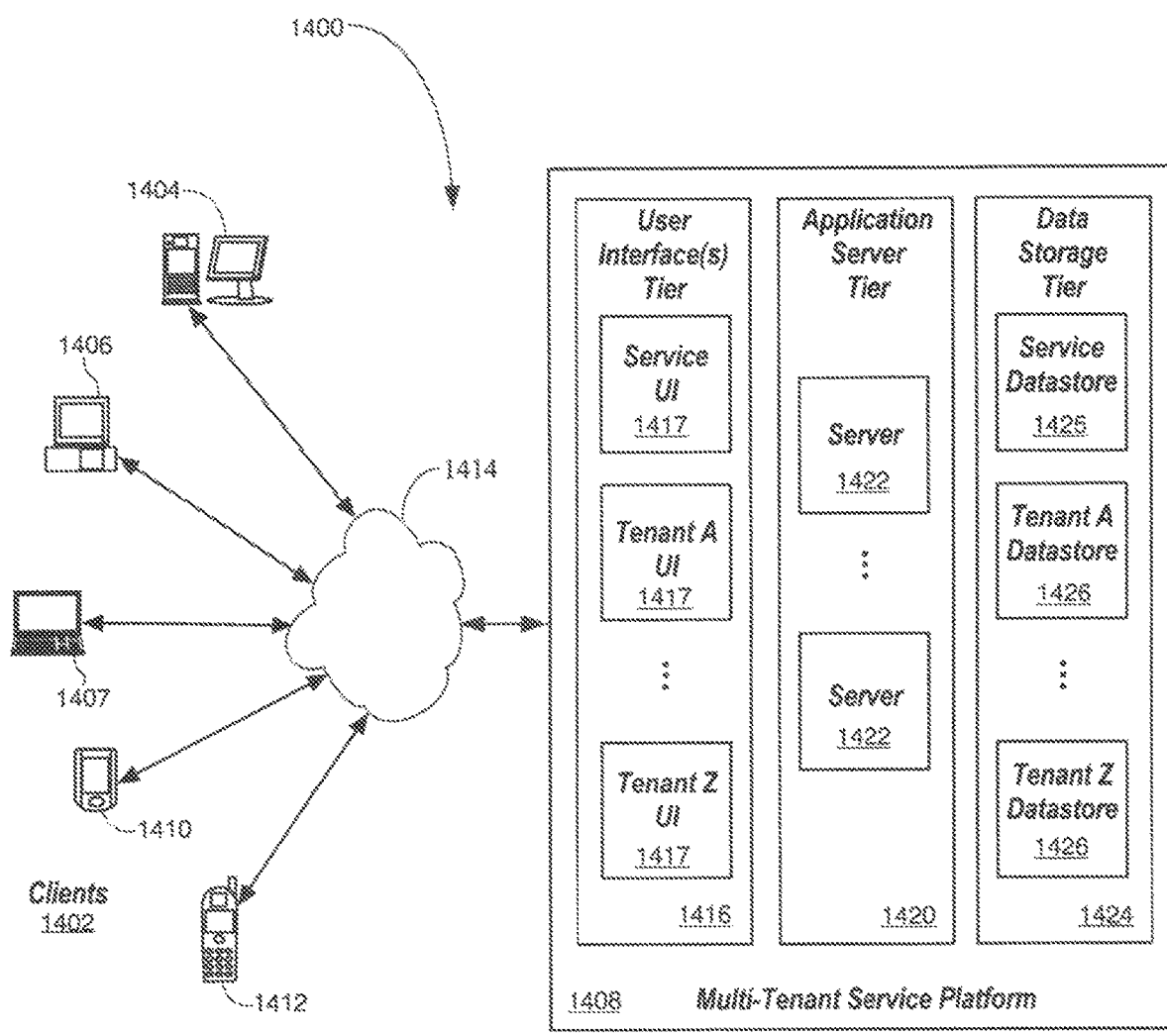
FIG. 14 illustrates elements or components of an example operating environment in which some embodiments described herein may be implemented.

FIG. 14 illustrates elements or components of an example operating environment 1400 in which embodiments described herein may be implemented. As illustrated, a variety of clients 1402 incorporating and/or incorporated into a variety of computing devices may communicate with a multi-tenant service platform 1408 through one or more networks 1414. For example, a client may incorporate and/or be incorporated into a client application (e.g., software) implemented at least in part by one or more of the computing devices. Examples of suitable computing devices include personal computers, server computers 1404, desktop computers 1406, laptop computers 1407, notebook computers, tablet computers or personal digital assistants (PDAs) 1410, smart phones 1412, cell phones, and consumer electronic devices incorporating one or more computing device components, such as one or more electronic processors, microprocessors, central processing units (CPU), or controllers. Examples of suitable networks 1414 include networks utilizing wired and/or wireless communication technologies and networks operating in accordance with any suitable networking and/or communication protocol (e.g., the Internet).

The distributed computing service/platform (which may also be referred to as a multi-tenant data processing platform) 1408 may include multiple processing tiers, including a user interface tier 1416, an application server tier 1420, and a data storage tier 1424. The user interface tier 1416 may maintain multiple user interfaces 1417, including graphical user interfaces and/or web-based interfaces. The user interfaces may include a default user interface for the service to provide access to applications and data for a user or "tenant" of the service (depicted as "Service UI" in the figure), as well as one or more user interfaces that have been specialized/customized in accordance with user specific requirements (e.g., represented by "Tenant A UI", . . . , "Tenant Z UI" in the figure, and which may be accessed via one or more APIs).

The default user interface may include user interface components enabling a tenant to administer the tenant's access to and use of the functions and capabilities provided by the service platform. This may include accessing tenant data, launching an instantiation of a specific application, causing the execution of specific data processing operations, etc. Each application server or processing tier 1422 illustrated in the figure may be implemented with a set of computers and/or components including computer servers and processors, and may perform various functions, methods, processes, or operations as determined by the execution of a software application or set of instructions. The data storage tier 1424 may include one or more data stores, which may include a Service Data store 1425 and one or more Tenant Data stores 1426. Data stores may be implemented with any suitable data storage technology, including structured query language (SQL) based relational database management systems (RDBMS).

Service Platform 1408 may be multi-tenant and may be operated by an entity to provide multiple tenants with a set of business-related or other data processing applications, data storage, and functionality. For example, the applications and functionality may include providing web-based access to the functionality used by a business to provide services to end-users, thereby allowing a user with a browser and an Internet or intranet connection to view, enter, process, or modify certain types of information. Such functions or applications are typically implemented by one or more modules of software code/instructions that are maintained on and executed by one or more servers 1422 that are part of the platform's Application Server Tier 1420. As noted with regards to FIG. 13, the platform system illustrated in FIG. 14 may be hosted on a distributed computing system made up of at least one, but typically multiple, "servers."

As mentioned, rather than build and maintain such a platform or system themselves, a business may utilize systems provided by a third party. A third party may implement a business system/platform as described above in the context of a multi-tenant platform, where individual instantiations of a business' data processing workflow (such as the data analysis and evaluation services and processing described herein) are provided to users, with each business representing a tenant of the platform. One advantage to such multi-tenant platforms is the ability for each tenant to customize their instantiation of the data processing workflow to that tenant's specific business needs or operational methods. Each tenant may be a business or entity that uses the multi-tenant platform to provide business services and functionality to multiple users.

Figure 15:
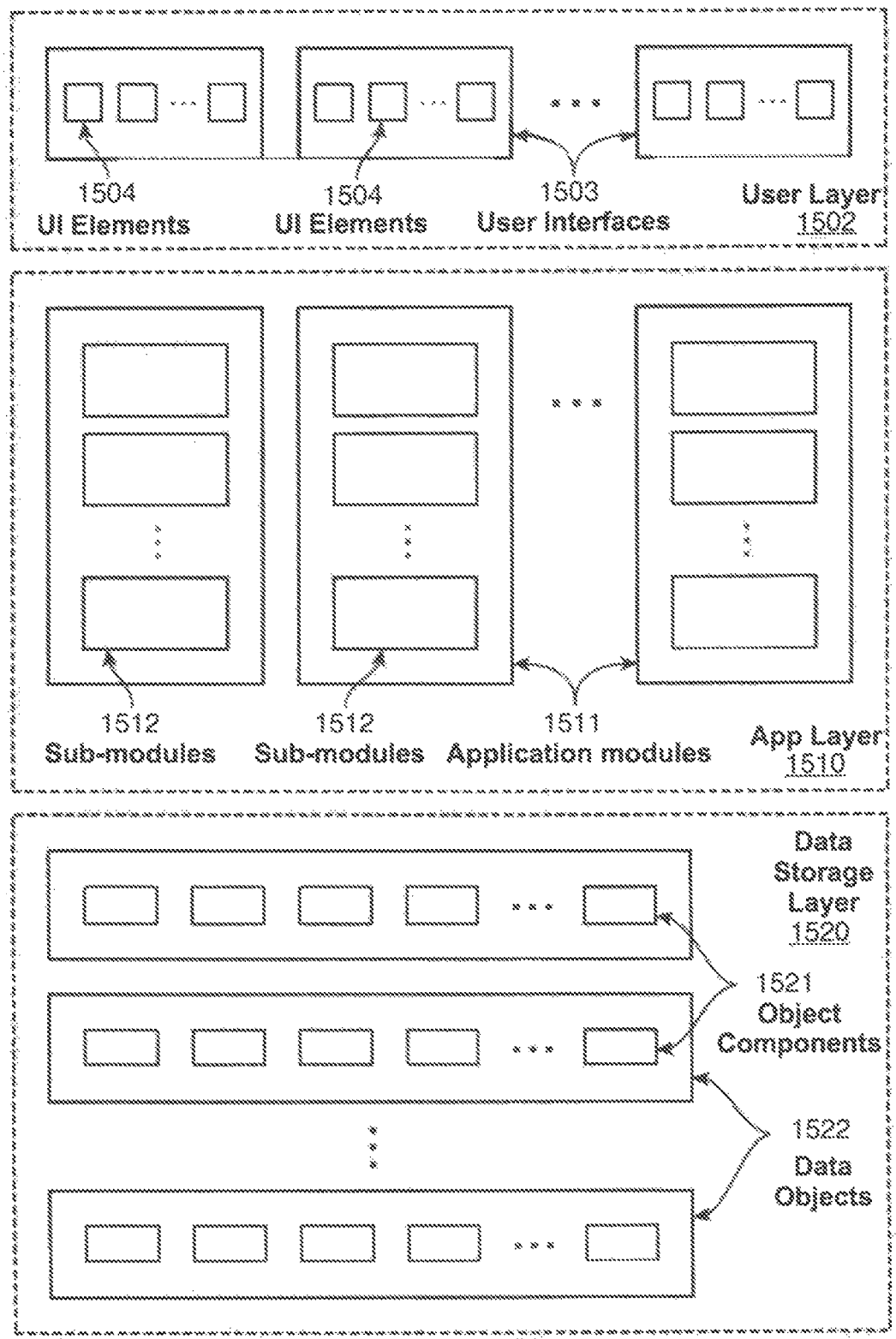
FIG. 15 illustrates some details of elements or components of a multi-tenant distributed computing service platform, of which some embodiments described herein may be implemented.

FIG. 15 illustrates additional details of the elements or components of the multitenant distributed computing service platform of FIG. 14, in which an embodiment may be implemented. The software architecture illustrated in FIG. 15 represents an example of an architecture which may be used to implement an embodiment. In general, an embodiment may be implemented using a set of software instructions that are designed to be executed by a suitably programmed processing element (such as a CPU, microprocessor, processor, controller, computing device, etc.). In a complex system such instructions are typically arranged into "modules" with each such module performing a specific task, process, function, or operation. The entire set of modules may be controlled or coordinated in their operation by an operating system (OS) or other form of organizational platform.

As noted, FIG. 15 is a diagram illustrating additional details of the elements or components 1500 of a multi-tenant distributed computing service platform, in which an embodiment may be implemented. The example architecture includes a user interface layer or tier 1502 having one or more user interfaces 1503. Examples of such user interfaces include graphical user interfaces and APIs. Each user interface may include one or more interface elements 1504. For example, users may interact with interface elements to access functionality and/or data provided by application and/or data storage layers of the example architecture. Examples of graphical user interface elements include buttons, menus, checkboxes, drop-down lists, scrollbars, sliders, spinners, text boxes, icons, labels, progress bars, status bars, toolbars, windows, hyperlinks, and dialog boxes. Application programming interfaces may be local or remote and may include interface elements such as parameterized procedure calls, programmatic objects, and messaging protocols.

The application layer 1510 may include one or more application modules 1511, each having one or more sub-modules 1512. Each application module 1511 or sub-module 1512 may correspond to a function, method, process, or operation that is implemented by the module or sub-module (e.g., a function or process related to providing business related data processing and services to a user of the platform). Such function, method, process, or operation may include those used to implement one or more aspects of the inventive system and methods, such as for one or more of the processes or functions described with reference to the figures.

The application modules and/or sub-modules may include any suitable computer-executable code or set of instructions (e.g., as would be executed by a suitably programmed processor, microprocessor, or CPU), such as computer-executable code corresponding to a programming language. For example, programming language source code may be compiled into computer-executable code. Alternatively, or in addition, the programming language may be an interpreted programming language such as a scripting language. Each application server (e.g., as represented by element 1422 of FIG. 14) may include each application module. Alternatively, different application servers may include different sets of application modules. Such sets may be disjoint or overlapping.

The data storage layer 1520 may include one or more data objects 1522 each having one or more data object components 1521, such as attributes and/or behaviors. For example, the data objects may correspond to tables of a relational database, and the data object components may correspond to columns or fields of such tables. Alternatively, or in addition, the data objects may correspond to data records having fields and associated services. Alternatively, or in addition, the data objects may correspond to persistent instances of programmatic data objects, such as structures and classes. Each data store in the data storage layer may include each data object. Alternatively, different data stores may include different sets of data objects. Such sets may be disjoint or overlapping.

Note that the example computing environments depicted in FIGS. 12-15 are not intended to be limiting examples. Further environments in which an embodiment may be implemented in whole or in part include devices (including mobile devices), software applications, systems, apparatuses, networks, SaaS platforms, IaaS (infrastructure-as-a-service) platforms, or other configurable components that may be used by multiple users for data entry, data processing, application execution, or data review.

Any of the software components, processes or functions described in this application may be implemented as software code to be executed by a processor using any suitable computer language such as Python, Java, JavaScript, C++ or Perl using conventional or object oriented techniques. The software code may be stored as a series of instructions, or commands in (or on) a non-transitory computer-readable medium, such as a random-access memory (RAM), a read only memory (ROM), a magnetic medium such as a hard-drive or a floppy disk, or an optical medium such as a CD-ROM. In this context, a non-transitory computer-readable medium is almost any medium suitable for the storage of data or an instruction set aside from a transitory waveform. Any such computer readable medium may reside on or within a single computational apparatus and may be present on or within different computational apparatuses within a system or network.

According to one example implementation, the term processing element or processor, as used herein, may be a central processing unit (CPU), or conceptualized as a CPU (such as a virtual machine). In this example implementation, the CPU or a device in which the CPU is incorporated may be coupled, connected, and/or in communication with one or more peripheral devices, such as display. In another example implementation, the processing element or processor may be incorporated into a mobile computing device, such as a smartphone or tablet computer.

The non-transitory computer-readable storage medium referred to herein may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, synchronous dynamic random access memory (SDRAM), or similar devices or other forms of memories based on similar technologies. Such computer-readable storage media allow the processing element or processor to access computer-executable process steps, application programs and the like, stored on removable and non-removable memory media, to off-load data from a device or to upload data to a device. As mentioned, with regards to the embodiments described herein, a non-transitory computer-readable medium may include almost any structure, technology, or method apart from a transitory waveform or similar medium.

Certain implementations of the disclosed technology are described herein with reference to block diagrams of systems, and/or to flowcharts or flow diagrams of functions, operations, processes, or methods. It will be understood that one or more blocks of the block diagrams, or one or more stages or steps of the flowcharts or flow diagrams, and combinations of blocks in the block diagrams and stages or steps of the flowcharts or flow diagrams, respectively, may be implemented by computer-executable program instructions. Note that in some embodiments, one or more of the blocks, or stages or steps may not necessarily need to be performed in the order presented or may not necessarily need to be performed at all.

These computer-executable program instructions may be loaded onto a general purpose computer, a special purpose computer, a processor, or other programmable data processing apparatus to produce a specific example of a machine, such that the instructions that are executed by the computer, processor, or other programmable data processing apparatus create means for implementing one or more of the functions, operations, processes, or methods described herein. These computer program instructions may also be stored in a computer readable memory that may direct a computer or other programmable data processing apparatus to function in a specific manner, such that the instructions stored in the computer-readable memory produce an article of manufacture including instruction means that implement one or more of the functions, operations, processes, or methods described herein.

Other objects and advantages of the systems and methods described will be apparent to one of ordinary skill in the art upon review of the detailed description and the included figures. Throughout the drawings, identical reference characters and descriptions indicate similar, but not necessarily identical, elements. While the exemplary embodiments described herein are susceptible to various modifications and alternative forms, specific embodiments have been illustrated by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

The use of the terms "a" and "an" and "the" and similar referents in the specification and in the following claims are to be construed to cover both the singular and the plural, unless otherwise indicated herein or clearly contradicted by context. The terms "having," "including," "containing" and similar referents in the specification and in the following claims are to be construed as open-ended terms (e.g., meaning "including, but not limited to,") unless otherwise noted. Recitation of ranges of values herein are merely indented to serve as a shorthand method of referring individually to each separate value inclusively falling within the range, unless otherwise indicated herein, and each separate value is incorporated into the specification as if it were individually recited herein. All methods described herein may be performed in any suitable order unless otherwise indicated herein or clearly contradicted by context. The use of any and all examples, or exemplary language (e.g., "such as") provided herein, is intended merely to better illuminate embodiments and does not pose a limitation to the scope of the embodiments unless otherwise claimed. No language in the specification should be construed as indicating any non-claimed element as essential to each embodiment.

As used herein (e.g., the claims, figures, and specification), the term "or" is used inclusively to refer items in the alternative and in combination.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments or examples are presented by way of examples for purposes of illustration and description. They are not intended to be exhaustive of or to limit this disclosure to the precise forms described. Many modifications and variations are possible in view of the above teachings. The embodiments or examples are illustrated and described in order to best explain the principles of this disclosure and practical applications, to thereby enable others skilled in the art to best utilize this disclosure and various embodiments or examples with various modifications as are suited to the particular use contemplated. It is intended that the scope of this disclosure be defined by the following claims and their equivalents.

We claim as follows:

1. A method of obtaining a physiological signal representing a patient metric, the method comprising:
   acquiring patient physiological data from a sensor operating in ambient conditions;
   generating a Photoplethysmography (PPG) signal or a pseudo PPG signal from the acquired patient physiological data, the PPG signal or the pseudo PPG signal having a signal quality characteristic associated with a quality indicator of the PPG signal or the pseudo PPG signal;
   comparing the signal quality characteristic of the PPG signal or the pseudo PPG signal to a correlating signal quality characteristic or parameter of a deep learning-based model PPG signal; and determining that the comparison of the signal quality characteristic of the PPG signal or the pseudo PPG signal to the signal quality characteristic or parameter of the deep-learning based model PPG signal does not meet a signal quality criterion.

2. The method of claim 1, further comprising adjusting in real-time a parameter of the ambient conditions, the adjusting based on the determination that the signal quality characteristic of the PPG signal or the pseudo PPG signal does not meet the signal quality criterion, wherein the ambient conditions include motion and lighting associated with the sensor.

3. The method of claim 1, further comprising, when the comparison of the signal quality characteristic of the PPG signal or the pseudo PPG signal to the signal quality characteristic or parameter of the model PPG signal does not meet the signal quality criterion, discarding the acquired patient physiological data, adjusting in real-time the ambient conditions, and acquiring new patient physiological data from the sensor.

4. The method of claim 1, further comprising, when the comparison of the signal quality characteristic of the PPG signal or the pseudo PPG signal to the signal quality characteristic or parameter of the model PPG signal does not meet the signal quality criterion:
discarding the acquired patient physiological data;
causing to display in real-time an indication of insufficient or improper sensor detection conditions; and
acquiring new patient physiological data from the sensor.

5. The method of claim 4, wherein the patient physiological data comprises metadata measured by an inertial measurement unit (IMU) of the mobile device.

6. The method of claim 5, wherein the indication of insufficient or improper sensor detection conditions is based, at least in part, on the metadata.

7. The method of claim 1, wherein acquiring the patient physiological data from the sensor further comprises capturing image frames using a camera of a mobile device.

8. The method of claim 7, wherein the image frames comprise images of at least a portion of a fingertip of a person.

9. The method of claim 8, wherein acquiring the patient physiological data from the sensor further comprises:
monitoring for problematic issues, in real-time, during the acquisition of the patient physiological data, wherein the problematic issues are based, at least in part, on relative motion between the fingertip and the camera.

10. The method of claim 9, wherein the relative motion between the fingertip and the camera is determined by an accelerometer of the mobile device.

11. The method of claim 9, wherein the relative motion between the fingertip and the camera is determined based, at least in part, on intensity measurements of pixel data of the image frames.

12. The method of claim 7, wherein generating the PPG signal or the pseudo PPG signal from the acquired patient physiological data comprises using a deep-learning model applied to one or more individual frames of the image frames.

13. The method of claim 7, wherein generating the PPG signal or the pseudo PPG signal from the acquired patient physiological data comprises using a deep-learning model applied simultaneously to at least two of the image frames.

14. The method of claim 7, wherein the image frames comprise red, green, blue (RGB) pixel data, and wherein the patient physiological data is based, at least in part, on the red pixel data.

15. The method of claim 7, wherein the image frames comprise a time-series of image frames that are partitioned into video chunks that each have a predetermined time span.

16. The method of claim 15, wherein two contiguous video chunks are combined into a video segment having a portion that comprises an overlap between the two contiguous video chunks.

17. The method of claim 15, wherein the deep-learning based model PPG signal is based, at least in part, on a neural network that is trained using transfer learning on pulse oximeter PPG data and information collected or produced by the mobile device, wherein the information includes the video chunks or blood pressure data previously determined by the mobile device.

18. The method of claim 1, wherein the sensor is a camera of a mobile device, and wherein acquiring the patient physiological data from the sensor further comprises controlling a flash of the mobile device.

19. The method of claim 1, wherein the sensor is a camera of a mobile device, and wherein acquiring the patient physiological data from the sensor further comprises controlling light sensitivity of the camera.

20. The method of claim 1, wherein the determining that the comparison of the signal quality characteristic of the PPG signal or the pseudo PPG signal to the correlating signal quality characteristic or parameter of the model PPG signal does not meet the quality criterion is performed by a process based on a trained blood pressure deep-learning based model.

* * * * *